United States Patent [19]

Clark et al.

[11] Patent Number: 5,111,817

[45] Date of Patent: May 12, 1992

[54] NONINVASIVE SYSTEM AND METHOD FOR ENHANCED ARTERIAL OXYGEN SATURATION DETERMINATION AND ARTERIAL BLOOD PRESSURE MONITORING

[75] Inventors: Justin S. Clark, Salt Lake City; William D. Wallace, Midvale, both of Utah

[73] Assignee: Medical Physics, Inc., Salt Lake City, Utah

[21] Appl. No.: 291,769

[22] Filed: Dec. 29, 1988

[51] Int. Cl.$^5$ .............................................. A61B 5/02
[52] U.S. Cl. .................................. 128/633; 128/664; 128/666; 128/667; 128/672; 356/41
[58] Field of Search ............... 128/633, 635, 664, 666, 128/667, 672, 675, 677, 679-683, 687-690; 356/41

[56] References Cited

U.S. PATENT DOCUMENTS

| | | | |
|---|---|---|---|
| 3,412,729 | 11/1968 | Smith | 128/633 |
| 4,266,554 | 5/1981 | Hamaguri | 128/633 |
| 4,446,871 | 5/1984 | Imura | 128/633 |
| 4,653,498 | 3/1987 | New, Jr. et al. | 128/633 |
| 4,685,464 | 8/1987 | Goldberger et al. | 128/633 |
| 4,714,080 | 12/1987 | Edgar, Jr. et al. | 128/666 |
| 4,759,369 | 7/1988 | Taylor | 128/664 |
| 4,770,179 | 9/1988 | New, Jr. et al. | 128/633 |
| 4,805,623 | 2/1989 | Jöbsis | 128/633 |
| 4,807,631 | 2/1989 | Hersch et al. | 128/666 |
| 4,825,872 | 5/1989 | Tan et al. | 128/633 |
| 4,825,879 | 5/1989 | Tan et al. | 128/633 |
| 4,832,484 | 5/1989 | Aoyagi et al. | 356/41 |
| 4,846,183 | 7/1989 | Martin | 128/633 |

FOREIGN PATENT DOCUMENTS 0227119 7/1987 European Pat. Off. ............ 128/666

Primary Examiner—Ruth S. Smith
Attorney, Agent, or Firm—Thorpe North Western

[57] ABSTRACT

A noninvasive system and method for monitoring arterial oxygen saturation levels which may also be used to continuously and noninvasively monitor blood pressure, including generating a continuous blood pressure waveform. The apparatus of the described embodiment includes a red LED and an infrared LED which are positioned to direct their respective light beams into, or reflected by a patient's body part. A phototransducer device is positioned to receive the light beams which are transmitted through the body part. A pressure cuff surrounds the body part and the LEDs. During calibration periods, pressure is applied to the body part and the systolic and mean blood pressures are determined and the arterial oxygen saturation level in the body part is determined. The pressure is then released from the body part and another arterial oxygen saturation level is determined and the difference between the two oxygen saturation levels is used as a calibration factor during later monitoring periods to remove the effect of nonarterial oxygen saturation levels on the values obtained during the subsequent monitoring period. The systolic and mean arterial pressures measured during a calibration period are used to develop a Hardy model compliance curve wherein the pressure-volume relationship of the arteries is determined. The modulation of the red LED light beam which strikes the photodetector, which corresponds to changes in arterial volume, can be used according to the Hardy model to continuously calculate a blood pressure waveform for the patient.

72 Claims, 9 Drawing Sheets

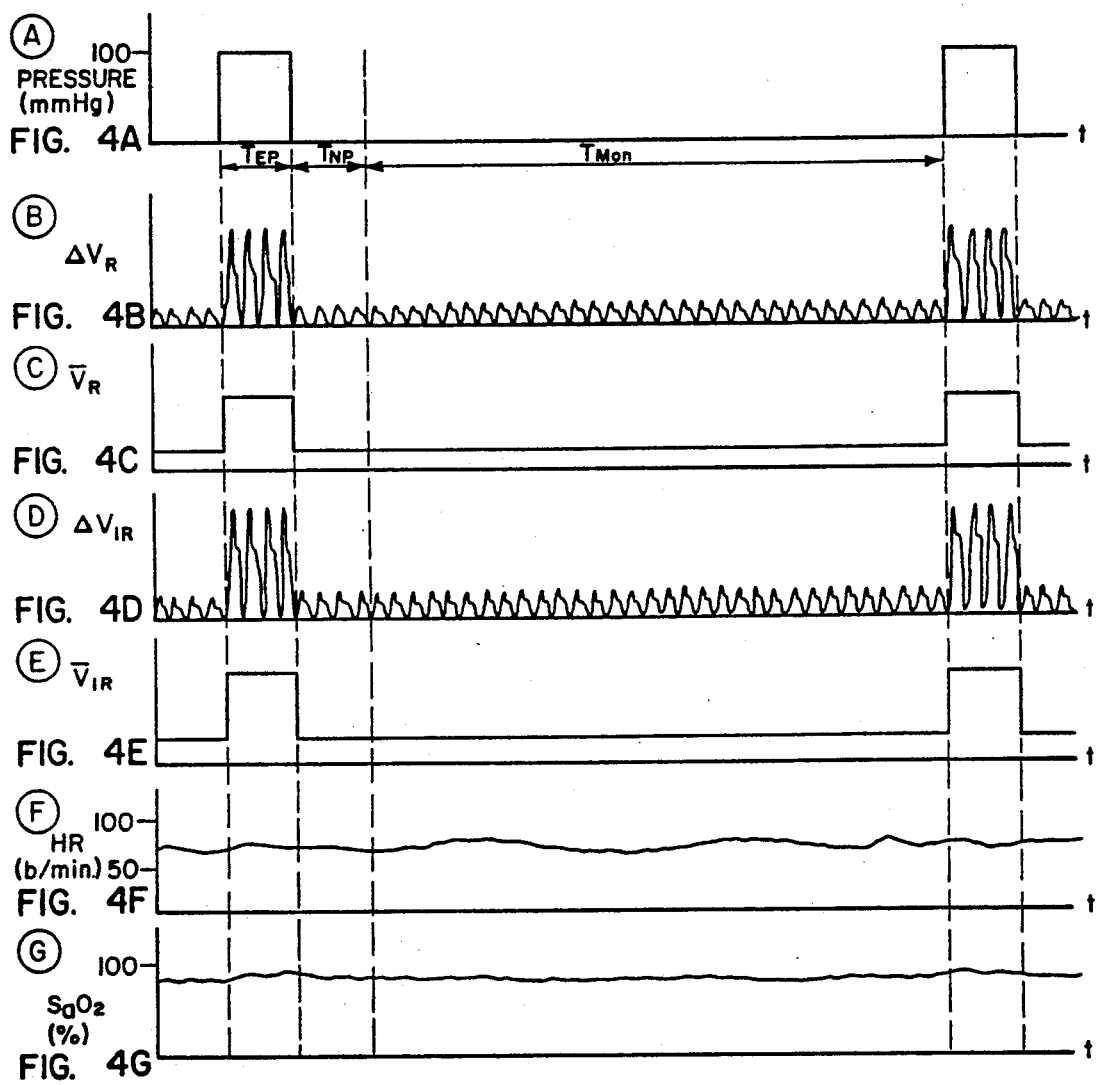

NONINVASIVE SYSTEM AND METHOD FOR ENHANCED ARTERIAL OXYGEN SATURATION DETERMINATION AND ARTERIAL BLOOD PRESSURE MONITORING

BACKGROUND

1. The Field of the Invention

The present invention is related to noninvasive systems and methods which are used to monitor the physiological condition of a patient's circulatory system. More particularly, the present invention is related to an enhanced noninvasive system and method for monitoring a patient's arterial oxygen saturation, and which also provides continuous measurement of blood pressure.

2. The Background Art

The proper utilization of many lifesaving medical techniques and treatments depends upon the attending physician obtaining accurate and continually updated information regarding various bodily functions of the patient. Perhaps the most critical information to be obtained by a physician, and that which will often tell the physician a great deal concerning what course of treatment should be immediately instituted, are heart rate, blood pressure, and arterial oxygen saturation.

In settings such as operating rooms and in intensive care units, monitoring and recording these indicators of bodily functions is particularly important. For example, when an anesthetized patient undergoes surgery, it is generally the anesthesiologist's role to monitor the general condition of the patient while the surgeon proceeds with his tasks. If the anesthesiologist has knowledge of the patient's arterial oxygen saturation, heart rate, and blood pressure, the general condition of the patient's circulatory system can be assessed.

Arterial oxygen saturation (abbreviated herein as $S_aO_2$) is expressed as a percentage of the total hemoglobin in the patient's blood which is bound to oxygen. The hemoglobin which is bound to oxygen is referred to as oxyhemoglobin. In a healthy patient, the $S_aO_2$ value is above 95% since blood traveling through the arteries has just passed through the lungs and has been oxygenated. As blood courses through the capillaries, oxygen is off-loaded into the tissues and carbon dioxide is on-loaded into the hemoglobin. Thus, the oxygen saturation levels in the capillaries (abbreviated herein as $S_cO_2$) is lower than in the arteries. Furthermore, the blood oxygen saturation levels in the veins is even lower, being about 75% in healthy patients.

Importantly, if the patient's arterial oxygen saturation level is too high or too low, the physician may take action such as reducing or increasing the amount of oxygen being administered to the patient. Proper management of $S_aO_2$ is particularly important in neonates where $S_aO_2$ must be maintained high enough to support cell metabolism but low enough to avoid damaging oxygen-sensitive cells in the eye and causing impairment or complete loss of vision.

Blood pressure monitoring includes at least three values which are of interest to a physician. First, the systolic pressure is the high pressure generated in the arteries during contraction (or systole) of the left ventricle of the heart. Second, the diastolic pressure is the pressure maintained in the arteries during relaxation (or diastole) of the left ventricle. Due to the elastic nature of the walls of the arteries, the diastolic pressure is above zero but less than the systolic pressure.

A third value of interest to a physician is the mean arterial pressure. The mean arterial pressure may be simply described as the arithmetic average of all the blood pressure values between, and including, the systolic and diastolic pressures. In addition to the just mentioned three discrete blood pressure values, a physician is also interested in obtaining the blood pressure waveform. As is well known, patients having identical systolic and diastolic values may have very different mean arterial pressures and their blood pressure waveforms may be dramatically different. Having the blood pressure waveform at hand allows the physician to more accurately assess the patient's condition.

Blood pressure is generally measured quantitatively in millimeters of mercury (mmHg) referenced against atmospheric pressure (about 760 mmHg). Thus, in a normal person the blood pressure may be 120 mmHg above atmospheric pressure during systole and 70 mmHg above atmospheric pressure during diastole. Such values are commonly recorded as "120 over 70" (120/70).

Continuous monitoring of arterial oxygen saturation levels ($S_aO_2$) and arterial blood pressures each present unique problems.

One method of determining $S_aO_2$ is to withdraw blood from an artery and analyze the same to determine the amount of oxyhemoglobin present. While in vitro analysis provides the most accurate blood gas determinations, the disadvantages of drawing a blood sample each time an $S_aO_2$ determination is desired by the physician is readily apparent. Significantly, even in the operating room in vitro $S_aO_2$ determinations may take up to several minutes. Since nerve cells deprived of sufficient oxygen begin to die in a matter of minutes, the time taken to obtain the results of an in vitro $S_aO_2$ analysis may seriously compromise patient safety.

Particularly in the case of a patient undergoing routine surgery, the difficulties of withdrawing blood samples throughout the surgical procedure for $S_aO_2$ determinations is generally too great to be adopted as a general practice. Still, monitoring of $S_aO_2$ during all surgeries where general anesthesia is used and in intensive care units is expected to have a significant positive effect on the well-being of patients. Thus, past efforts have been directed to providing noninvasive systems and methods for determining arterial $S_aO_2$.

The term "oximetry" has been adopted in the art to refer to noninvasive apparatus and methods for determining blood oxygen saturation levels. Previously available oximetry systems make use of the fact that the absorption characteristics of different blood components, namely, $HbO_2$ and Hb and also referred to as the coefficient of extinction, differ depending upon which wavelength of light (e.g., infrared or visible portions of the spectrum) is being used.

Thus, previously available noninvasive oximetric systems impinge at least both visible and infrared light upon a body part, such as a finger, and then estimate the $SO_2$ level using the relative proportions of visible and infrared light which was transmitted or reflected. Undesirably, such systems inherently include some inaccuracy, which increases to a substantial error for low (50-70%) $SO_2$ levels, due to, among other things, the inclusion of capillary blood as well as arterial blood in the reading.

In an effort to improve the accuracy of the $SO_2$ values obtained using only two wavelengths of light, rather than the bulky and expensive ear oximeter previously available, which impinged light of eight different wavelengths on the body part, other apparatus have utilized the pulsatile component of the transmitted or reflected light beam to distinguish variations in the detected intensity of the light beam which are due to changes in blood components from other causes. Generally referred to as pulse oximetry, using the pulsatile signal modulating the light beams for $S_aO_2$ estimate provides a significant improvement in accuracy over nonpulse oximetry systems yet still does not distinguish between arterial blood oxygen saturation and capillary blood oxygen saturation.

The previously available systems and methods of monitoring blood pressure also all have a variety of disadvantages. The most commonly performed method, the auscultatory sphygmomanometer method (utilizing a pressure cuff, mercury manometer, and a stethoscope), often provides reasonable estimates of systolic and diastolic blood pressure. But the method does not provide any information concerning the mean blood pressure or the pressure waveform. Moreover, a trained professional must take one or more minutes to carry out the method and even then may be unsuccessful.

Arterial catheterization provides very accurate blood pressure measurements and waveforms in critical care situations. The extreme invasiveness and the risks of catheterization, including infection, thrombus formation, hemorrhage, and cerebral embolization precludes the method from being routinely used on patients.

In an attempt to provide noninvasive blood pressure monitoring devices, several methods have been suggested in the past. Devices incorporating a constantly inflated finger cuff which tracks the pressure changes within the finger disadvantageously may cause pain to the patient, interference with the pressure measurement, and/or tissue damage.

In an effort to avoid the disadvantages of using a constantly inflated pressure cuff, various devices utilizing photoplysmography have been introduced. While such devices utilize a light beam directed at the finger, or other body part, to sense changes in blood vessel volume in order to determine changes in pressure and thus avoid the use of a constantly inflated pressure cuff, such devices still suffer from inaccurate readings, particularly when determining the diastolic pressure, and such devices still cannot provide an accurate representation of the arterial pressure waveform.

In view of the disadvantages and drawbacks of the previously available apparatus and methods, it would be an advance in the art to provide a system and method for noninvasively measuring arterial blood oxygen saturation levels while minimizing the effect of capillary oxygen saturation on the measurement. It would be another advance to provide a system for measuring both arterial oxygen saturation levels and blood pressure using no more hardware than necessary to measure oxygen saturation. It would also be an advance in the art to provide a system and method for noninvasively measuring blood oxygen saturation levels and blood pressure which minimizes contact with, and the pressure applied to, the body of the patient. It would be a further advance in the art to provide a system for noninvasive blood oximetry or blood pressure monitoring which may be applied to any one of several parts of the patient's body.

It would also be an advance in the art to provide both a method and system for blood oximetry and blood pressure monitoring which may be implemented using little specialized hardware. It would be yet another advance in the art to provide a noninvasive blood pressure monitoring system and method which can provide systolic, diastolic, and mean arterial pressure measurements as well as an accurate representation of the pressure waveform. Still another advance in the art would be to provide a noninvasive system and method for measuring arterial blood oxygen saturation levels which enhances the arterial contribution and reduces the influence of the capillary contribution to the oxygen saturation measurement.

OBJECTS AND BRIEF SUMMARY OF THE INVENTION

In view of the prior state of the art, it is a primary object of the present invention to provide a noninvasive system and method to determine arterial blood oxygen saturation levels while minimizing the interference of the capillary blood oxygen saturation levels with the determination of arterial blood oxygen saturation levels.

Another object of the present invention is to implement a noninvasive system and method for carrying out arterial blood oximetry which is more accurate than previously available apparatus and methods and which is also capable of being used on more than one body part of the patient.

It is another object of the present invention to provide a system and method which allows both blood pressure monitoring and blood oximetry to be concurrently carried out by the same apparatus. Still another object of the present invention is to provide a system and method for noninvasive blood oximetry which can be operated in both a transmission and reflection mode and can be backed on any one of a plurality of body parts.

It is a still further object of the present invention to provide a noninvasive blood oximetry and blood pressure monitoring system and method which does not require that pressure be applied to the patient's body during the monitoring interval and that occlusive pressure is applied for only brief durations during calibration intervals.

Yet another object of the present invention is to provide a noninvasive system and method for both blood oximetry and accurately determining a patient's systolic, diastolic, and mean arterial blood pressure and displaying the patient's blood pressure waveform.

Additional objects and advantages will be apparent from the description which follows, or may be learned by the practice of the invention.

Consistent with the foregoing objects, the present invention provides a noninvasive system and method for enhanced monitoring of arterial oxygen saturation ($S_aO_2$) which may be used alone or in combination with a method for continuously and noninvasively monitoring blood pressure. When used, the monitoring of blood pressure provides determinations of systolic pressure, diastolic pressure, mean arterial pressure, and perhaps most significantly, producing an accurate arterial pressure waveform. Most advantageously, the present invention allows the same hardware to be used for both monitoring of arterial oxygen saturation and monitoring of arterial blood pressure.

The apparatus of the presently preferred embodiment of the present invention includes a light means comprising two or more light emitting devices which are positioned to direct at least two light beams into a body part of the patient. The two light beams are comprised of two different wavelengths, preferably a reference light beam, which is absorbed substantially equally by both oxyhemoglobin and reduced hemoglobin, preferably having a wavelength in the infrared portion of the spectrum and a measurement light beam, which is absorbed unequally by oxyhemoglobin and reduced hemoglobin, preferably having a wavelength in the visible red portion of the spectrum. Other portions of the spectrum may also be used within the scope of the claimed invention.

Also provided is a detection means, transducer means, or a photodetector which detects the amount of the light beams which are absorbed by the blood. The detection means and equivalent devices may be positioned to detect either the light transmitted through, or reflected by, the body part.

Importantly, the visible red light beam which will be transmitted or reflected will vary according to the ratio of oxyhemoglobin ($HbO_2$), to reduced hemoglobin (Hb) in the blood. Oxyhemoglobin is the component of blood responsible for carrying almost all of the oxygen to the body tissues. In contrast, the intensity of the detected infrared light beam will not vary significantly with the ratio of $HbO_2$ to Hb. This is due to the fact that the amount of infrared light absorbed by the body part is affected relatively little by the changing proportions of $HbO_2$ and Hb.

In accordance with the present invention, an enhancement means is provided to increase the arterial contribution of the pulsatile component of the light beams which are detected by the phototransducer means. The enhancement means comprises a pressure means for imposing an increased pressure on the body part.

With each heartbeat the volume of the arteries varies slightly which modulates the intensity of the detected light beams. The pulsatile component may also be referred to as the "AC component" of the light beam "signal." The pulsatile component is impressed upon a relatively steady light beam "signal" referred to as the "DC" "signal." The importance of the pulsatile component is known to those skilled in the art and will be further explained later in this disclosure.

The enhancement means operates by applying an increased enhancement pressure onto the body part into which the light beams are directed. By applying an enhancement pressure to the body part, the enhancement pressure being approximately equal to the mean arterial pressure of the major artery or arteries located in the body part, the arterial pulsatile component of the light beam detected by the phototransducer means will be maximized due to unloading of the transluminal pressure which results in maximizing arterial compliance. Generally, the increase in the pulsatile component will be about an order of magnitude greater than the pulsatile component of the detected light beams without application of the enhancement pressure.

Importantly, application of the enhancement pressure decreases the relative contribution of the capillary blood oxygen saturation ($S_cO_2$) to the intensity of the detected light beams. Thus, the increased enhancement pressure both increases the modulation of the light beam due to the increase in amplitude of the arterial pulses and by reducing the amount of capillary blood in the body part.

The imposition of the enhancement pressure on the body part may be considered a "physiological calibration." Having carried out such a "physiological calibration" by enhancing the contribution of the pulsatile arterial oxygen saturation level to the light detected by the phototransducer means, a processor means, for example a microprocessor or other computing device, may derive a calibration factor representing the contribution of the capillary oxygen saturation to the total light detected by the phototransducer means.

The processor means, or microprocessor, controls the operation of the system to carry out the method of the present invention to completion and thus continually updates and displays the arterial oxygen saturation level of the patient on a display means such as a video monitor. The enhancement pressure may be imposed by a device such as an inflatable pressure cuff, accompanied by a controllable pressure pump, adapted for placement on a finger, forehead, or some other body part.

The enhancement pressure is only applied during a first interval of the calibration period. During a second interval of the calibration period, the enhancement pressure is released and a calibration factor is obtained which reflects the ratio of $S_aO_2$ to $S_cO_2$. After the calibration period is completed, the monitoring period is begun and the calibration information is used to determine the proportion of the pulsatile signal detected by the phototransducer means which is caused by the arterial oxygen saturation level rather than the capillary oxygen saturation level.

The present invention also includes utilizing the above described hardware for continual blood pressure monitoring and waveform display. The pressure monitoring function is carried out by determining the mean arterial pressure and the systolic blood pressure using the oscillometric method. In the oscillometric method the mean arterial pressure is determined by adjusting the inflation of a pressure cuff placed around a body part until the pulsatile signal is maximized. Once the amplitude of the pulsatile signal is maximized, the pressure within the cuff is approximately equal to the mean arterial pressure.

The oscillometric method determines the systolic pressure by increasing the pressure applied to a body part to above the systolic pressure, i.e., completely occluding the artery so that no pulsatile signal is present, and then gradually reducing the pressure within the cuff until a pulsatile signal appears, providing a data point which can be used to calculate the patient's systolic pressure using a procedure described herein.

Advantageously, the present invention also provides for calculation of a complete pressure waveform and diastolic pressure. With the mean arterial pressure and the systolic pressure being known, the present invention allows the change in volume of the artery, which is proportional to the pressure within the artery, to be detected by the phototransducer means as a modulation of the intensity of the measurement (red or infrared) light beam directed into the body part.

The pressure-volume relationship of an artery is not linear or the same from patient to patient or from hour to hour. The pressure-volume relationship of the patient's artery may be described and predicted using a model known as the "Hardy model compliance curve." The information needed to determine the pressure-volume relationship, including the systolic pressure and the mean arterial pressure, are obtained using the oscillometric method during the calibration period when the pressure cuff is inflated in the below-described manner.

During the monitoring period, the pressure within the cuff is released and the volume change in the artery is detected by the phototransducer means. The present invention then uses a recursive procedure wherein an estimated diastolic pressure and the Hardy model compliance curve is used to derive a calculated mean arterial pressure. If the difference between the calculated mean arterial pressure and the measured mean arterial pressure is within a predetermined standard, then the estimated diastolic pressure is displayed on the display means as the patient's diastolic pressure. If the calculated mean arterial pressure and the measured mean arterial pressure do not agree within predetermined limits, a new estimated diastolic pressure is chosen and the calculations repeated until the estimated diastolic pressure produces a calculated mean arterial pressure substantially the same as the measured mean arterial pressure.

As the diastolic blood pressure is being calculated, three parameters required to determine the pressure-volume relationship in the artery using the Hardy model are being calculated. The three parameters include:

$k =$ compliance index for the arterial blood vessels of the patient;
$V_m =$ maximum volume of the arterial blood vessels in the patient's body part; and
$V_0 =$ volume of the arterial blood vessels in the patient's body part at zero pressure Importantly, using the described method, the value of any point on a blood pressure waveform between the systolic and diastolic pressures may be calculated. Thus, a continuous and complete blood pressure waveform may be generated using the method. The ability to calculate a complete and accurate representation of the patient's arterial blood pressure waveform is a great advance over previously available systems using photoplethysmography.

Further information concerning the pressure monitoring function of the present invention will be provided later in this disclosure as well as being provided in U.S. patent application Ser. No. 07/068,107 (now U.S. Pat. No. 4,846,189) entitled "Noncontactive Arterial Blood Pressure Monitor and Measuring Method" filed on Jun. 29, 1987, which is incorporated herein by reference.

As will be more fully appreciated during a description of the remainder of this disclosure, the blood oximetry functions of the present invention may be carried out alone or a system can be designed to carry out the oximetry function as well as the blood pressure monitoring function without requiring any hardware in addition to that used to carry out the oximetry function of the present invention.

BRIEF DESCRIPTION OF THE DRAWINGS

FIGS. 4a–4g are waveform diagrams showing the application and release of pressure on the patient's body by the pressure cuff of the described embodiment and its effect on the detected light beams.

DETAILED DESCRIPTION OF THE PREFERRED EMBODIMENTS

Reference will now be made to the drawings to describe the presently preferred embodiment of the present invention. While the embodiment described herein performs both blood oxygen saturation and blood pressure monitoring functions, a system carrying out only the blood oxygen saturation monitoring function may be constructed if desired. Furthermore, the described embodiment is only illustrative of one of the many possible embodiments for carrying out the present invention.

Continuous transportation of oxygen to the cells of the body is essential to the well-being of the patient. Nearly all of the oxygen transported from the lungs to the rest of the body is carried by hemoglobin stored in the erythrocytes or red blood cells. As hemoglobin releases carbon dioxide and combines with oxygen its color changes from cyan to a bright red. Arterial oxygen saturation ($S_aO_2$) is expressed as a percentage of the maximum oxygen which the arterial blood can carry. An oxygen saturation level of about 95%–98% is considered normal in most patients.

Significantly, both hemoglobin and oxyhemoglobin have approximately the same absorption coefficient for light in the infrared portion of the spectrum. However, the absorption coefficients of the two compounds is very different for red light in the visible portion of the spectrum. The difference in absorption coefficients allow $S_aO_2$ to be measured noninvasively using two light beams of two appropriate and differing wavelengths. It should be appreciated that the phrase "light beam" as used herein is intended to include any electromagnetic radiation having an appropriate wavelength which is directed toward, or impinged upon, the patient's body regardless of whether the light beam is collimated or uncollimated, coherent or incoherent.

Figure 1:
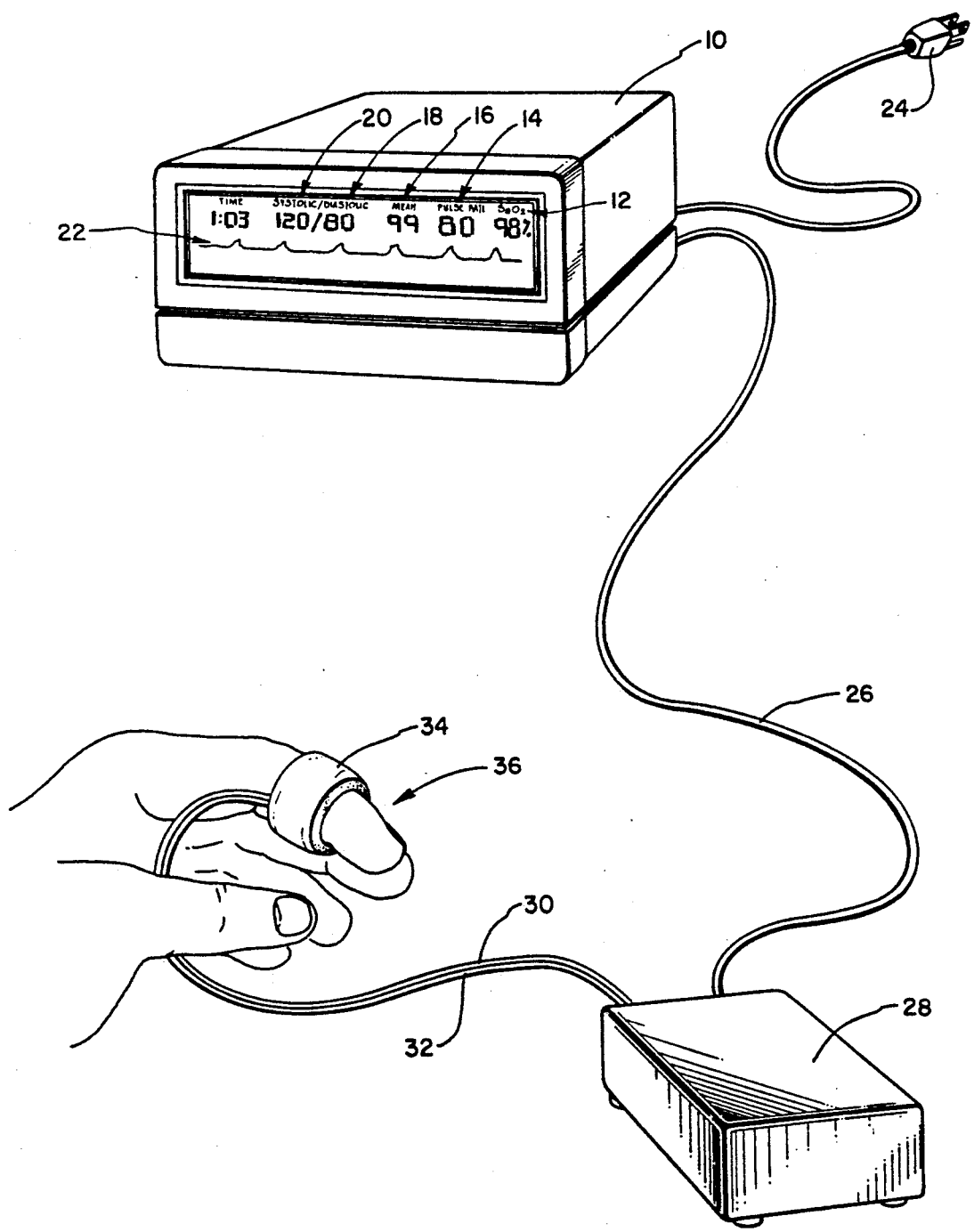
FIG. 1 is a perspective view of the presently preferred embodiment of the present invention which is configured to provide both blood pressure monitoring and arterial oxygen saturation monitoring functions.
Figure 2:
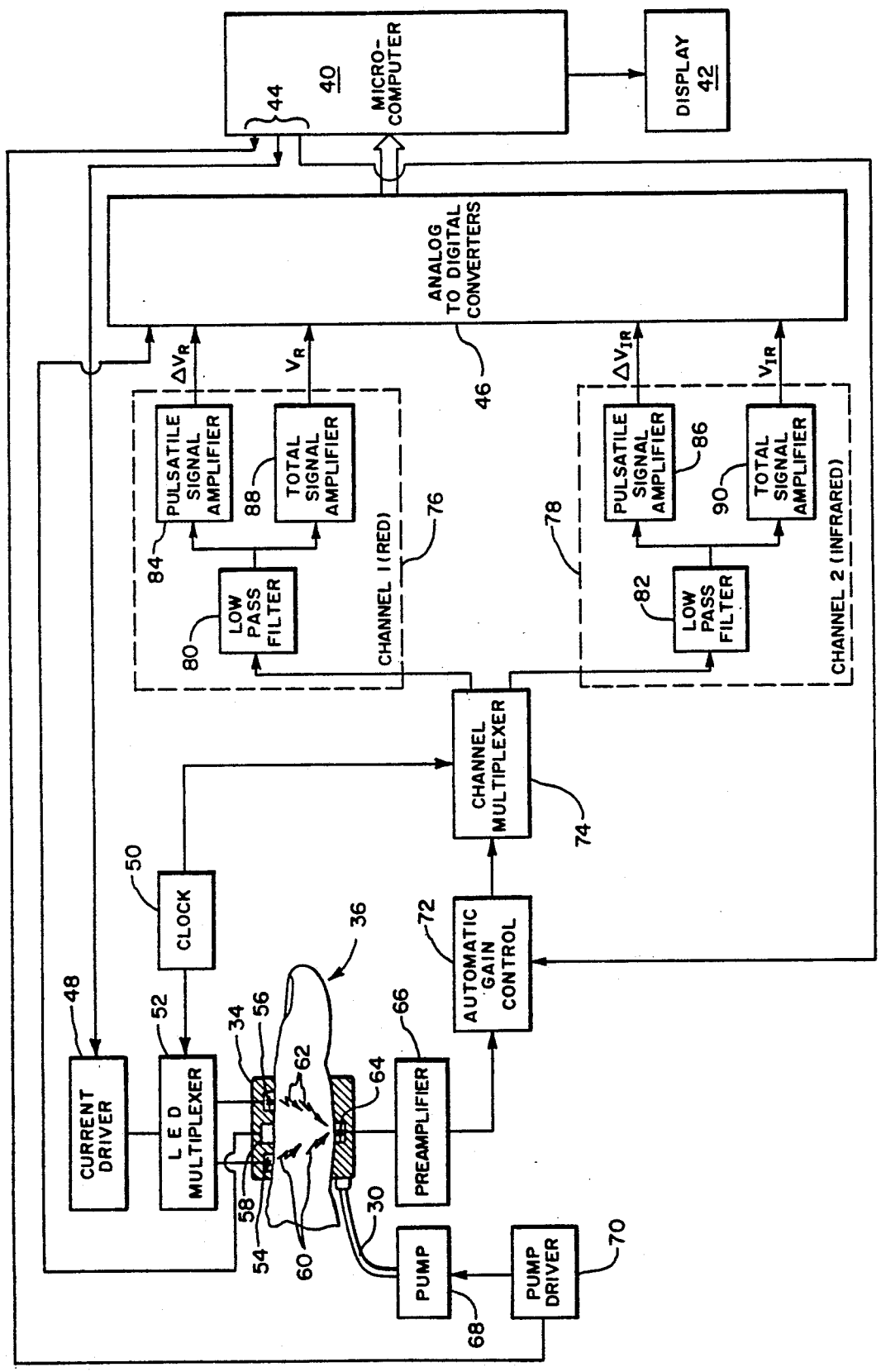
FIG. 2 is a block diagram of the system of the presently preferred embodiment of the present invention.

FIG. 1 provides a perspective view of the major components of the described embodiment including a micro computer 10, a visual display 12, a pump 28 (incorporating a pump driver), a finger cuff 34 (incorporating a pressure cuff, light emitting diodes, and a phototransducer), as well as cables 26 and 30, and tubing 32 interconnecting the components. It will be appreciated that components which are equivalent to many of the functional blocks represented in FIG. 2 are contained within the structures illustrated in FIG. 1 and thus are not separately represented in FIG. 1.

Shown in FIG. 1 is a patient's finger 36 and the presently preferred embodiment of the present invention being used to determine the patient's $S_aO_2$ level at the numerical display represented generally at 12. The patient's blood pressure is also being monitored with the systolic, mean, and diastolic blood pressure values being provided at numerical displays represented generally at 20, 18, and 16, respectively. The patient's blood pressure waveform is also being shown on the visual display indicated at 22.

The illustrated embodiment, as well as other embodiments of the present invention, have application in many circumstances. Such circumstances may include patients undergoing anesthesia during surgery, critical and intensive care units, exercise and sleep studies, as well as other applications.

In FIG. 1 the sensing elements of the embodiment, including the pressure cuff 34 which surrounds the light emitting diodes, the photodetector, and the pressure transducer, are located between the first and second knuckle of the patient's index finger. While this position is illustrated for purposes of describing the presently preferred embodiment, other positions on the body may be used in specific circumstances as will be discussed later. Also, the specific arrangement of the sensing elements in relation to the body part will be described as appropriate in the description of the preferred embodiment.

FIG. 2 illustrates the major functional blocks of the embodiment illustrated in FIG. 1 and described herein. It is to be understood that the hardware represented by the functional blocks illustrated in FIG. 2 may be implemented in many different ways.

In the presently preferred embodiment, the microcomputer may be a general purpose microcomputer 40 such as an IBM Personal Computer or an equivalent device. Alternatively, it may be desirable to utilize a more powerful microcomputer or to devise a microprocessor-based apparatus specifically designed to carry out the data processing functions incidental to this invention. When choosing a microcomputer, if both the blood oximetry and the blood pressure monitoring (including waveform display) are to be carried out and displayed in real time, the microcomputer 40 or other processor means must carry out a large number of computations very quickly.

Importantly, the hardware which embodies the processor means of the present invention must function to perform the operations essential to the invention and any device capable of performing the necessary operations should be considered an equivalent of the processor means. As will be appreciated, advances in the art of modern electronic devices may allow the processor means to carry out internally many of the functions carried out by hardware illustrated in FIG. 2 as being independent of the processor means. The practical considerations of cost and performance of the system will generally determine the delegation of functions between the processor means and the remaining dedicated hardware.

As can be seen in FIG. 2, in the presently preferred embodiment microcomputer 40 is interconnected with the remaining apparatus hardware by way of I/0 ports 44 and a plurality of analog to digital converters 46. Also, a visual display 42 is connected to the microcomputer 40.

Visual display 42 performs the function of a display means. As intended herein, the display means may be any device which enables the operating personnel to observe the values and waveforms calculated by the microcomputer. Thus, the display means may be a device such as a cathode ray tube, an LCD display, a chart recorder, or any other device performing a similar function.

The method of the present invention is carried out under the control of a program resident in the microcomputer. Those skilled in the art, using the information given herein, will readily be able to assemble the necessary hardware, either by purchasing it off-the-shelf or by fabricating it and properly program the microcomputer in either a low level or a high level programming language. While it is desirable to utilize clock rates that are as high as possible and as many bits as possible in the A/D converters 46, the application of the embodiment and economic considerations will allow one skilled in the art to choose appropriate hardware for interfacing the microcomputer with the remainder of the embodiment. Also, it should be understood that for reasons of simplifying the diagrams, power supply connections, as well as other necessary structures, are not explicitly shown in the figures, but are provided in actuality using conventional techniques and apparatus.

As represented in FIG. 2, an LED current driver 48 is provided. The LED current driver 48 controls the amount of current directed to the infrared LED and the red LED. Since LEDs are current controlled devices, the amount of current passed through the devices determines, within device limits, the intensity of the light beam emitted thereby.

Schematically shown in FIG. 2 is a side view of a patient's finger 36 with the pressure cuff 34 shown in cross section, also referred to as the enhancement means, which surrounds the finger. Disposed on the interior of the pressure cuff are the infrared LED 56, the red LED 54, and a photodiode 64.

Both the infrared LED 56 and the red LED 54 may be devices which are commonly available in the semiconductor industry. They provide high power outputs and relatively stable operation at a reasonable cost per device. The red LED 54 preferably emits a light beam having a wavelength of 660 nanometers (also preferably in the range from about 600 to about 725 nanometers) and the infrared LED 56 preferably emits a light beam having a wavelength of 930 nanometers (also preferably in the range from about 875 to about 1,000 nanometers).

Light emitting devices other than those mentioned above could be used and are intended to be within the scope of the inventive concepts claimed herein. The light emitting devices may be placed outside of the pressure cuff 34 with a fiber optic pathway provided to the interior of the pressure cuff. Furthermore, other wavelengths of light may be used as suitable devices for generating such wavelengths become available.

As used herein, the phrase light means is intended to include the above-mentioned LEDs as well as any devices which perform functions equivalent to those performed by the LEDs. As will be appreciated by considering the foregoing discussion, any source or sources of light capable of emitting light having two differing and appropriate wavelengths may function as the light means. Thus, for example, unitary light emitting devices capable of emitting two or more wavelengths of light, or devices emitting wavelengths of light other than those specified above, are within the intended scope of the phrase structure defined by light means.

The photodiode 64 disposed within the pressure cuff 34 is preferably one having a spectral response which is substantially equal at the wavelengths emitted by the infrared LED 56 and the red LED 54 and which, like the LEDs, is capable of stable operation over a long period of time. It may be desirable to include a temperature sensing device (not shown) adjacent the LEDS and the photodiode to provide the microcomputer 40 data on the temperature dependent variations in the operations of LEDs 54 and 56 and the photodiode 64. It is preferable that the LEDs and the photodiode be readily replaceable so that any drift which occurs in the operating parameters of the devices (possibly due to the effects of aging) may be remedied by replacing old components with new ones.

The functions carried out by photodiode 64 may be best labeled by the phrases detection means, light detection means, and transducer means. Importantly, any device which performs the function of detecting the amount of light transmitted through, or reflected from, a body part and creating an electrical signal of some kind which contains information on the intensity of the light striking the device may function as the detection means, light detection means, or transducer means. As will be appreciated by those skilled in the art, phototransducers such as phototransistors and many other devices now available, or available in the future, have application within the scope of the present invention. Methods for determining arterial blood oxygen levels using either light beams passed through, or reflected from, a body part will be described later in this disclosure.

It is presently preferred that the LEDs 54 and 56 be positioned about the finger so that the light beams pass through the digital arteries on each side of the phalanx bone. Thus, the arterial blood's contribution to the modulation of the light beams is maximized rather than the light beams being absorbed by tissue and bone. Also, rather than having a single LED located on each side of the phalanx bone, a pair of LEDs, each pair including a red LED and an infrared LED, may be positioned immediately adjacent each other. Each pair of LEDs is positioned on the interior of the pressure cuff so that the respective light beams pass through one of the arteries located on each side of the phalanx bone of the finger. This provides that both an infrared and a red light beam will be equally modulated by the same artery.

Also represented in FIG. 2 is a pressure transducer 58. The pressure transducer 58 is used when determining the patient's blood pressure but is not necessary to the blood oximetry function of the present invention. Pressure transducer 58 acts as a pressure detection means or a pressure transducer means and functions to generate an electrical signal which is proportional to the pressure being imposed upon the body part by the pressure cuff. Thus, any device performing the same, or an equivalent function, should be considered a pressure detection means or pressure transducer means.

Alternatively, rather than locating the sensing elements on the patient's finger, the sensing elements may be located on body parts such as on a toe, ear, the web of the hand, or over the temporal artery on the patient's forehead. Of course, each of these locations will require a different arrangement for the pressure cuff or other structure for imposing the enhancement pressure.

In particular, locating the sensing structures over the temporal artery on the forehead requires that the LEDs and photodiode be positioned so that the photodiode senses the light beams which are reflected from, rather than transmitted through, the body part. Furthermore, a structure other than a pressure cuff must be used to apply pressure to the temporal artery and to hold the pressure imposing device in place. Still, the temporal artery may be the most preferred location for the sensing structures in many cases due to the fact that perfusion at the temporal artery is affected less by vascular disease and drugs than the arteries found in the extremities. Thus, use of the temporal artery may provide more accurate $S_aO_2$ determinations than a location on a patient's extremities, in some cases.

As shown in FIG. 2, an LED multiplexer 52, driven by a clock 50, alternately connects the current driver 48 to either the infrared LED 56 or the red LED 54. The operation of the clock 50 and the LED multiplexer 52 ensures that only one of either the red LED 54 or the infrared LED 56 will operate at one time. The output of clock 50 is also input to channel multiplexer 74 to provide synchronized operation.

The pressure cuff 34 should be opaque so that the photodiode 64 is shielded from any stray ambient light. The pressure cuff 34 is inflated and deflated by a pump 68 which operates under the control of the pump drive 70 which is in turn controlled by the microcomputer 40.

As suggested earlier, if the embodiment is to be used only for determinations of $S_aO_2$, the pump 68 need only be capable of inflating the pressure cuff 34 to a pressure equal to the mean arterial pressure. If the embodiment is to be used to also determine blood pressure, the pump 68 should be capable of inflating the pressure cuff 34 to a pressure well above the patient's systolic pressure so that the arteries may be completely occluded and the systolic pressure determined as explained earlier.

The pressure cuff 34, pump 68, and pump driver 70 comprise the enhancement means or pressure means of the present invention. As will be appreciated from the previous discussion concerning the application of mean arterial pressure on an artery and its effect on the arterial pulsatile signal, any structure which functions to partially or fully occlude a patient's artery should be considered the equivalent of the enhancement means or pressure means. The body part which is used as a sensing location will often dictate the best devices and structures used as the enhancement or pressure means.

As illustrated in FIG. 2, a preamplifier 66 receives the output of the photodiode 64. The preamplifier 66 boosts the photodiode output to a level usable by the automatic gain control (AGC) 72. The automatic gain control 72 functions to limit the dynamic range of the voltage signal output from the preamplifier 66 to that which is appropriate for the circuits which follow.

The gain-controlled output from the AGC 72 is applied to a channel multiplexer 74 which is also driven by the clock 50. Thus, when the LED multiplexer 52 causes the red LED 54 to operate, the output of the AGC 72 is directed to Channel 1 (red) as represented at 76 in FIG. 2. Conversely, when the LED multiplexer 52 causes the infrared LED 56 to operate, the output of the AGC 72 is directed to Channel 2 (infrared) as represented at 78 in FIG. 2.

Each channel 76 and 78 includes a low pass filter 80 and 82 to reduce high frequency (e.q., $\geq 40$ Hz) noise. The signal output from each of the low pass filters 80 and 82 is applied to pulsatile signal amplifiers 84 and 86, respectively, which include high-pass filters to prevent passage of direct current and very low frequencies (e.g., $\geq 1$ Hz). Thus, the pulsatile signal amplifiers 84 and 86 can be thought of as AC amplifiers. The output of the pulsatile signal amplifiers provide $\Delta V_{IR}$ signal and $\Delta V_R$ signal to the microprocessor by way of the A/D converters 46. The and $\Delta V_{IR}$ and $\Delta V_R$ signals reflect only the AC, i.e., pulsatile, component of the light beams passed through the patient's body part.

The total signal amplifiers 88 and 90, one provided for each channel, are not frequency limited and thus pass to their outputs an amplified waveform containing both the DC and AC components of the $V_{IR}$ and $V_R$ signals which were output from the low pass filters 80 and 82, respectively.

With the hardware assembled as illustrated in FIG. 2, data concerning all of the variables which must be considered to determine both the patient's $S_aO_2$ level and blood pressure is presented to the microcomputer for processing according to the method of the present invention. In summary, the microcomputer 40 controls the intensity of the LEDs 54 and 56, the inflation of the pressure cuff 34, and the gain of the output from the photodiode 64. The microcomputer receives as input data, the $\Delta V_{IR}$ and $\Delta V_R$ signals (pulsatile component of the signals) and the $V_{IR}$ and $V_R$ signals (the total signals including both the AC and DC components).

Figure 3A:
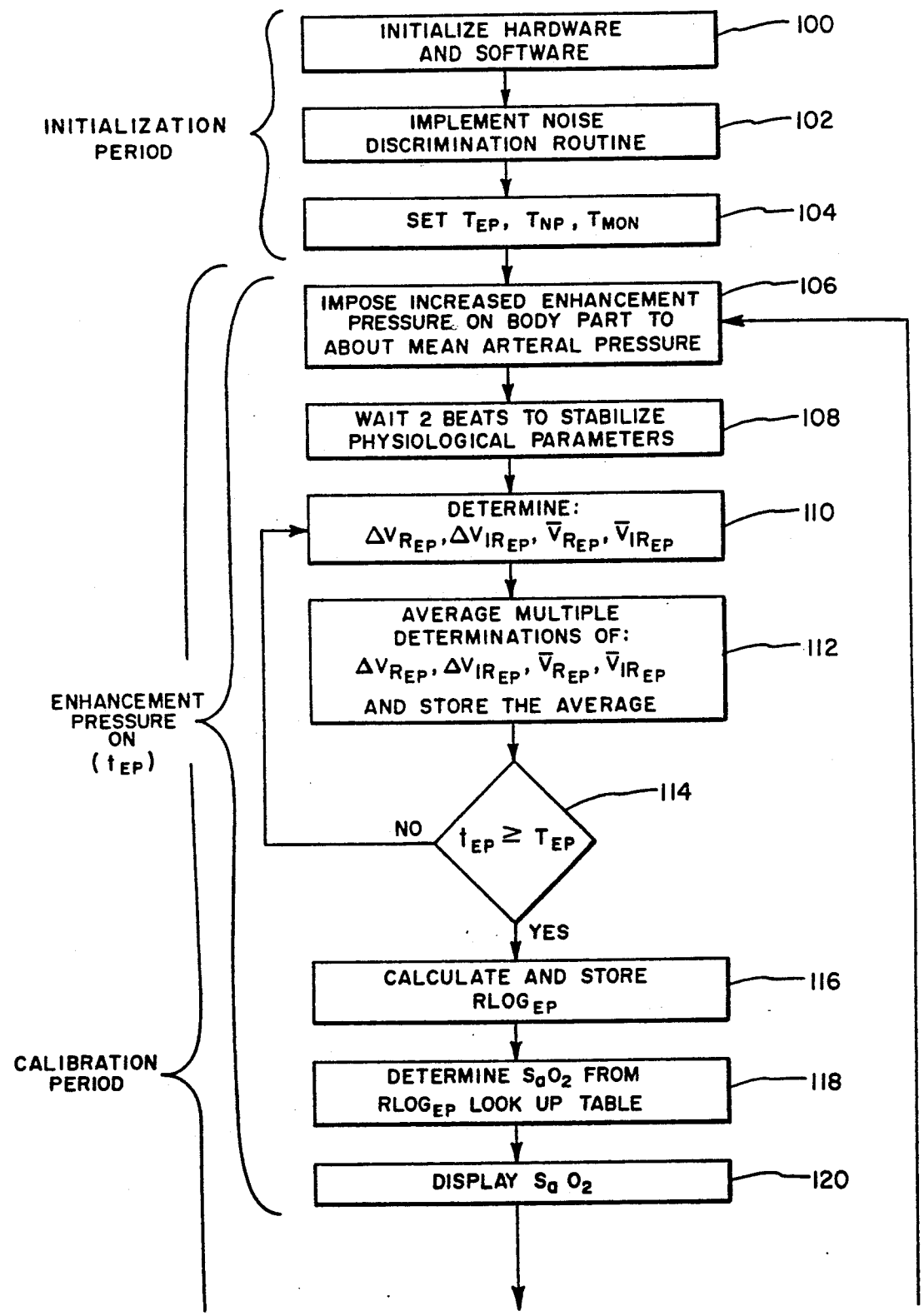
FIGS. 3A and 3B are flow charts representing the steps of one presently preferred method of the present invention for determining arterial blood oxygen saturation levels.
Figure 3B:
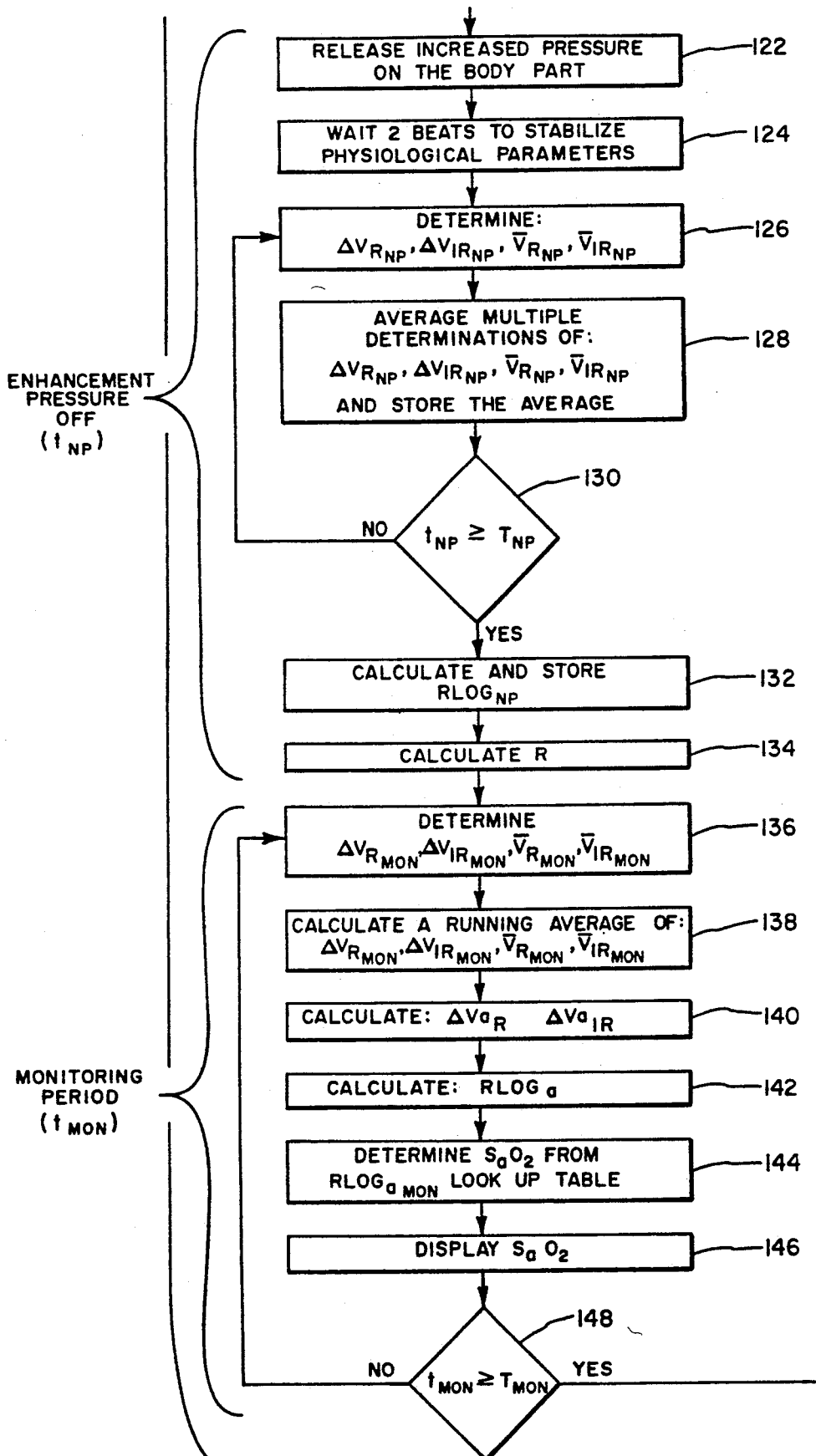

The presently preferred method of the present invention is carried out by the system illustrated in FIG. 2 and comprises those steps illustrated in the flow chart of FIG. 3. In order to explain one method of the preferred embodiment, FIGS. 3A and 3B will be used with reference to the waveform diagrams of FIG. 4 as well as the block diagram of FIG. 2.

The flow chart of FIGS. 3A and 3B represents just one of the many embodiments which may be used to carry out the method defined in the claims. Particularly, with the widespread availability of powerful microprocessors, the present invention requires little specialized hardware and the data acquisition and manipulations steps described herein may be varied and yet still be within the scope of the invention as defined in the claims. In order to clarify the following description, the blood oximetry function of the present invention will first be explained and then the combination of the blood oximetry function and the blood pressure monitoring function will be explained.

It should be noted that the flow chart of FIG. 3 is divided into three principal periods: the initialization period; the calibration period; and the monitoring period. Furthermore, the calibration period is divided into an enhancement pressure-on interval when the enhancement pressure is applied to the patient's body part and an enhancement pressure-off interval when the enhancement pressure is not applied.

Briefly, the steps carried out during the initialization period include those pertaining to determining certain set up parameters, and implementing any software routines which must be running while data is being acquired. The steps carried out during the calibration period include imposing an increased enhancement pressure on the body part, acquiring data, determining the $S_aO_2$ with the enhancement pressure on, and then with the enhancement pressure off, continuing to acquire data which can be used to determine a "physiological calibration factor" which is used during the monitoring period. During the monitoring period no pressure is applied to the body part and further data is obtained to determine the patient's $SO_2$ level. The data previously acquired and the resulting calculated values are used according to the method described herein to determine the $S_aO_2$ level during the monitoring period.

As shown in the flow chart of FIGS. 3A and 3B, the method of the present invention begins during the initialization period with the initialization of the hardware and software of the system as represented at step 100. Those skilled in the application of microprocessors to medical monitoring situations will understand the various software routines which should be run after power is applied, but before data is acquired. For example, as represented at step 102, it is very desirable to implement a conventional noise discrimination routine.

In the present case, such a noise discrimination routine may be one known to those skilled in the art which includes an algorithm to distinguish information associated with each pulse and heart beat from noise, which in the present system, may be due to ambient light temporarily striking the photodiode or artifacts in the signals caused by motion of the patient. During such a noise discrimination routine, the patient's heart rate will be determined and may be displayed for the information of the attending medical professional.

As mentioned earlier, the calibration period includes an "enhancement pressure-on interval" and an "enhanced pressure-off interval" which is followed by a monitoring period. The length of each of these periods ($T_{EP}$, $T_{NP}$, and $T_{MON}$, respectively) are determined at step 104 according to the criteria discussed below. While not represented in the flow chart of FIG. 3A, in some embodiments it may be desirable to include a software routine which will vary $T_{EP}$, $T_{NP}$, and $T_{MON}$ according to the physiological condition of the patient.

It is known that application of pressure on a body part which causes even partial occlusion of blood vessels and capillaries to some extent has an effect on perfusion in the body part. Significantly, if pressure is applied to a body part long enough, the actual blood pressure found in the blood vessels will begin to change due to changes in the blood vessels involved. Furthermore, determinations of $S_aO_2$ become more difficult and less reliable the longer the pressure is applied. Moreover, from the view point of the unanesthetized patient, application of pressure on a body part will result in pain.

Thus, it is important that the time that the enhancement pressure is imposed be limited to avoid pain in the unanesthetized patient and in all patients to avoid altering the patient's blood pressure and $S_aO_2$. In general cases, $T_{EP}$ will be less than or equal to about 0.2 to about 0.5 of the sum of $T_{NP}$ and $T_{MON}$ resulting in a pressure imposed duty cycle of less than about 20% to about 50%.

With the above considerations in mind, it is necessary to determine how long the calibration period ($T_{EP}+T_{NP}$) should be in relation to the length of the monitoring period which will also determine how often the steps of the calibration period are carried out. Importantly, the calibration period must be long enough to allow accurate data to be collected. Additionally, since physiological parameters change over time, and may change rapidly due to stress, injury to the patient, drugs, or other treatment administered to the patient, the steps of the calibration period must be carried out regularly.

For example, if a patient's condition is rapidly changing and the patient is unconscious, it may be desirable to carry out the steps of the calibration period for as long as the steps of the monitoring period are carried out in order to obtain the most accurate and constantly updated information to the attending physician. Moreover, in many patients suffering from vascular disease, poor perfusion may cause reliable $S_aO_2$ determinations to be available only when the enhancement pressure is imposed upon the body part.

Once the initialization period steps have been completed, the enhancement pressure is applied to the body part as represented at step 106. As explained earlier, the enhancement pressure may be applied to one of several body parts containing a significant artery. As explained earlier, the imposition of the enhancement pressure accomplishes two primary results: Increasing the amplitude of the AC (or pulsatile) component of the arterial pulse component of the transmitted (or reflected in the case of the method represented in FIGS. 5A and 5B) light beams; and Decreasing the absorption of the light beams by blood in the capillaries increasing the amplitude of the AC (or pulsatile) component of the arterial pulse of the artery. Both of these results allows more accurate noninvasive $S_aO_2$ determinations than previously possible. Such accurate $S_aO_2$ determinations are even possible under conditions of relatively low perfusion. As will now be recognized, the enhancement pressure is so named because the contribution of the arterial blood to the $SO_2$ determination is enhanced.

The result of increasing the amplitude of the pulse of the artery is brought about by the well known effect that the amplitude of the blood pressure pulses is maximized as the pressure imposed upon the artery equals the mean arterial pressure. The increase in artery pulses, i.e., the pulsatile signal detected by the system, allows more accurate $S_aO_2$ determinations even under conditions of low perfusion. Because the difference between $S_aO_2$ and $S_cO_2$ may vary dramatically from patient to patient and from hour to hour, the "physiological calibration" carried out by the present invention is essential to improving the accuracy of $S_aO_2$ determinations.

In practice, it is not necessary for the blood oximetry system to hold the enhancement pressure at exactly the mean arterial pressure for the entire enhancement pressure-on interval. As shown in FIGS. 4a–4g at waveform A, when the enhancement pressure is increased to, for example, 100 mmHg (assuming the mean arterial pressure is 100 mmHg) the pulsatile signals $\Delta V_R$ and $\Delta V_{IR}$ (waveforms B and D, respectively) increase by about an order of magnitude. Thus, the enhancement pressure need only be about equal to the mean arterial pressure to cause the desired increase in the pulsatile signals ($\Delta V_R$ and $\Delta V_{IR}$).

Rather than holding the enhancement pressure exactly on the mean arterial pressure, it may be useful to slowly ramp the enhancement pressure (e.g., 5 mmHg/sec), particularly when a ramping pressure must be imposed to accurately determine the mean arterial pressure for use in blood pressure.

As shown at step 108 in FIG. 3A, after the enhancement pressure has been imposed, it is generally necessary to wait at least two heart beats so that the physiological parameters can stabilize after changing the pressure imposed upon the body part. Once the physiological parameters have stabilized, it is necessary to determine values for the following variables as shown at 110 in FIG. 3:

$\Delta V_{REP}$= the pulsatile signal output from the photodiode when the red LED is operating during the enhancement pressure-on interval $\Delta V_{IREP}$= the pulsatile signal output from the photodiode when the infrared LED is operating during the enhancement pressure-on interval $\overline{V}_{REP}$= the average of the total signal output from the photodiode when the red LED is operating during the enhancement pressure-on interval $\overline{V}_{IREP}$= the average of the total signal output from the photodiode when the infrared LED is operating during the enhancement pressure on interval The $\Delta V_{REP}$ and $\Delta V_{IREP}$ are input to the microcomputer by way of the appropriate channel amplifiers and analog to digital converters. The $\overline{V}_{REP}$ and $\overline{V}_{IREP}$ values are calculated by the microcomputer by the data received from the total signal amplifiers 88 and 90 and the analog to digital converters 46. FIG. 4 provides representative waveforms suggesting relative values of the listed variables.

In practice, the waveforms are not continuous but are time division multiplexed with Channel 1 (the red channel) and Channel 2 (the infrared channel) each having a voltage from the photodiode gated to the channel amplifiers an equal amount of time. However, the gating of the output of the photodiode is not represented in waveforms B, C, D, and E in order to increase the clarity of the waveforms. Moreover, the operation of the clock represented in FIG. 2 desirably may be synchronized with the operation of the analog-to-digital converters and also should be fast enough that a very accurate representation of the waveforms may be preserved.

Each of these waveforms is represented in FIGS. 4a–4g. As shown at waveforms B and D during $T_{EP}$, the $\Delta V_{REP}$ and $\Delta V_{IREP}$ waveforms include only the AC or pulsatile component of the photodiode signal as processed by, and output from, the pulsatile signal amplifiers of each channel. The $\overline{V}_{REP}$ and the $\overline{V}_{IREP}$, represented by waveforms C and E, respectively, of FIG. 4, are an average, or more specifically a mean, of the total signal output from the photodiode.

It will be appreciated that in the described embodiment the signal output from photodiode 64 will be expressed and processed in terms of a voltage, hence the label "V."

In particular, the $\overline{V}_{REP}$ and the $\overline{V}_{IREP}$ signals are not directly measured but are determined mathematically by the microcomputer hardware and software from the signal output from the total signal amplifiers 88 and 90 of each channel and digitized by the analog-to-digital converters 46.

It will be appreciated that much of the signal processing hardware may be eliminated by assigning more of the signal processing to the microcomputer without departing from the spirit and essential characteristics of the system and method of the present invention. Nevertheless, in order to arrive at an appropriate balance between speed of operation, flexibility, accuracy, and cost of the system, the dedicated hardware, such as the amplifiers 84, 86, 88, and 90, which is illustrated and described is preferably included in the system.

Next, as represented at step 112, the average (mean) of multiple determinations of $\Delta V_{REP}$, $\Delta V_{IREP}$, $\overline{V}_{REP}$, and $\overline{V}_{IREP}$ are each calculated and stored until the elapsed time of the enhancement pressure on interval ($t_{EP}$) is equal to or greater than the preset enhancement pressure interval $T_{EP}$, as represented at step 114. It will be realized that in some circumstances it may be desirable to express $T_{EP}$, and the other periods and intervals discussed herein, in terms of the number of heartbeats which have occurred rather than on a set period of time. Still further, it may be useful in some cases to include algorithms in the embodied method of the present invention which may switch between using heartbeats and set time periods for the intervals and which may also vary the length, whether time or heartbeats, of the intervals.

Each average determined from the $\Delta V_{REP}$, $\Delta V_{IREP}$, $\overline{V}_{REP}$ and $\overline{V}_{IREP}$ signals are individually stored in the microcomputer's memory.

Next, as shown at Step 116, a value for $RLOG_{EP}$ using equation (1) is determined using the stored average values:

$$RLOG_{EP} = \frac{\log(1 + \Delta V_{REP}/\overline{V}_{REP})}{\log(1 + \Delta V_{IREP}/\overline{V}_{IREP})} \quad (1)$$

Equation (1) is applied to a data obtained by transmitting the light beams through a body part since the transmission of light through whole blood only somewhat follows the Lambert-Beers law. Equation (1) requires that the log of the pertinent values be calculated. This equation is familiar to those skilled in the art and may be easily carried out by the microcomputer.

However, since transmission of light through whole blood results in values which deviate significantly from the Lambert-Beers law once a value for $RLOG_{EP}$ is calculated and stored, the $S_aO_2$ corresponding to the $RLOG_{EP}$ value is found by reference to a $RLOG_{EP}$ look-up table as indicated at step 118. The $RLOG_{EP}$ look up table is derived from empirical data gathered during use of the system described herein. For example, once a red LED, infrared LED, photodiode, and other hardware items have been configured to provide the system described herein, the values obtained for $RLOG_{EP}$ may be correlated with the $S_aO_2$ value obtained using another $S_aO_2$ determination method, for example, an in vitro method. Alternatively, the subject's $S_aO_2$ may be altered by altering the composition of the inspired gases and monitoring the composition of the expired gases. Once the look-up table has been completed, it can be used in the case of any number of patients if the performance of the apparatus hardware is maintained within appropriate parameters considering the effects of age, temperature, and variability of mass produced components.

The $S_aO_2$ which was determined from the $RLOG_{EP}$ look-up table at step 118 is displayed as represented at step 120 in FIG. 3 on the display means 42 represented in FIG. 2. It should be appreciated that the $S_aO_2$ value displayed at step 120 during the enhancement pressure on interval is more accurate and reliable than $SaO_2$ values provided by previously available pulse oximetry systems due to the enhancement of the arterial pulsatile signal output from the photodiode and the decrease of the capillary oxygen saturation contribution to the same signal.

Nevertheless, the interval during which the enhancement pressure is imposed must be limited due to several considerations including avoiding pain for the patient and affecting the physiology of the patient so that the measurements obtained are altered in any significant fashion. Thus, the enhancement pressure is released from the body part for the remainder of the calibration period and monitoring period as represented at step 122 as shown in FIG. 3B.

As shown in FIGS. 4a–4g, the enhancement pressure-off interval of the calibration period begins when the enhancement pressure is released and the pressure on the body part returns to the ambient pressure. Again, as represented at step 124, it is necessary to wait at least two heartbeats before measuring any variables.

Continuing to refer to FIG. 3B and similarly to the steps taken during the enhancement pressure-on interval, the enhancement pressure-off interval includes steps to determine four variables as shown at Step 126.

$\Delta V_{RNP}=$ the pulsatile signal output from the photodiode when the red LED is operating during the enhancement pressure-off interval $\Delta V_{IRNP}=$ the pulsatile signal output from the photodiode when the infrared LED is operating during the enhancement pressure-off interval $\overline{V}_{RNP}=$ the average of the total signal output from the photodiode when the red LED is operating during the enhancement pressure-off interval $\overline{V}_{IRNP}=$ the average of the total signal output from the photodiode when the infrared LED is operating during the enhancement pressure-off interval Also, similarly to the steps taken during the enhancement pressure-on interval, the average of multiple determinations of the enhancement pressure-off interval variables (step 128) is calculated until the length of the enhancement pressure-off interval ($t_{NP}$) is equal to or greater than the time previously set for the enhancement pressure-off interval ($T_{NP}$) as represented at step 130 in FIG. 3B.

A value for $RLOG_{NP}$ is then obtained as represented at step 132 in accordance with equation (2) shown below:

$$RLOG_{NP} = \frac{\log(1 + \Delta V_{RNP}/\overline{V}_{RNP})}{\log(1 + \Delta V_{IRNP}/\overline{V}_{IRNP})} \quad (2)$$

Then, having calculated and stored both $RLOG_{EP}$ and $RLOG_{NP}$, R may be calculated according to equation (3) below:

$$R = (RLOG_{EP}/RLOG_{NP})C \quad (3)$$

Where C is a calibration function given by equation (4) below:

$$C = F(SO_2)_{NP}/F(SO_2)_{EP}F(SO_2)_{EP} \quad (4)$$

where:

$F(SO_2)_{NP}=$ the inverse of the look-up table function for functional oxygen saturation without the enhancement pressure imposed $F(SO_2)_{EP}=$ the inverse of the look-up table function for functional oxygen saturation with the enhancement pressure imposed Thus, C in equation (4) represents a calibration factor which must be introduced to maintain accuracy of the system because of the differences, which may be very small, between the look-up tables for $RLOG_{EP}$ and $RLOG_{MON}$. Having calculated R in accordance with equation (3), corrections can be made to subsequent $S_aO_2$ measurements to account for the effect of $S_cO_2$ and to reduce or eliminate the contribution of $S_cO_2$ on the $S_aO_2$ determination leaving just the $S_aO_2$ level to be displayed to the physician. Having carried out these steps, the calibration period is completed.

The first step in the monitoring period ($t_{MON}$) shown at 136 in FIG. 3B, requires that the values for the following variables be determined:

$\Delta V_{RMON}=$ the pulsatile signal output from the photodiode when the red LED is operating during the monitoring period $\Delta V_{IRMON}=$ the pulsatile signal output from the photodiode when the infrared LED is operating during the monitoring period $\overline{V}_{RMON}=$ the average of the total signal output from the photodiode when the red LED is operating during the monitoring period $\bar{V}_{IRMON}$ = the average of the total signal output from the photodiode when the infrared LED is operating during the monitoring period Next, at step 138, a running average of the four variables is calculated. It may be desirable to allow the physician using the system of the present invention to determine how heavily past values for the four variables will be weighted in subsequent calculations.

As will be appreciated, weighing previously obtained determinations of the four variables will result in a displayed $S_aO_2$ value which is more immune to motion artifacts, noise, and spurious signals but which is less responsive to rapid changes in $S_aO_2$ levels. Alternatively, if the previously obtained values for the four variables are weighted little or not at all, in $S_aO_2$ levels. Alternatively, if the previously obtained values for the four variables are weighted little or not at all, then the system will be very responsive to rapid changes in $S_aO_2$ levels but motion artifacts, noise, and supurious signals may cause the display of an occasional inaccurate $S_aO_2$ value. When such an inaccurate $S_aO_2$ value is displayed, the physician will need to judge whether the display is an accurate reflection of the patient's condition or is caused by sources other than the patient's $S_aO_2$ levels.

Next as shown at step 140, values for $\Delta Va_r$ and $\Delta Va_{IR}$ are calculated according to equations (5) and (6), provided below:

$$\Delta Va_R = \Delta V_R(1-aR) \qquad (5)$$

$$\Delta Va_{IR} = \Delta V_{IR}(1-aR) \qquad (6)$$

where a equals the capillary pulse volume fraction.

Next, at step 142, $RLOG_a$ is calculated according to equation (7):

$$RLOG_a = \frac{\log(1 + \Delta Va_R/\bar{V}_R)}{\log(1 + \Delta Va_{IR}/\bar{V}_{IR})} \qquad (7)$$

Having calculated $RLOG_a$, the $S_aO_2$ level may be determined by obtaining a value from the $RLOG_{aMON}$ look-up table as represented at step 144. The $RLOG_{aMON}$ look-up table is derived empirically in a fashion similar to that described earlier for the $RLOG_{EP}$ look-up table. Significantly, the value obtained from the $RLOG_{aMON}$ look-up table represents the $S_aO_2$ value since the $S_cO_2$ contribution has already been "calibrated out" by the steps used to arrive at $RLOG_a$. The value obtained from the $RLOG_{aMON}$ look-up table is displayed as indicated at step 146. The steps of the monitoring period are repeated until $t_{MON} \geq T_{MON}$ as shown at step 148.

Alternative steps may be substituted to or added to the method of the invention without departing from its intended scope. For example, it is possible to arrive at a calibration factor by comparing the $F(SO_2)_{EP}$ and $F(SO_2)_{NP}$ values to determine what percentage of the $SO_{2MON}$ value represents the $S_aO_2$ level. However, the above described steps are presently preferred in order to obtain the most accurate $S_aO_2$ determinations when the photodetection means is configured to operate in a transmission mode such as is the case in the embodiment represented in FIG. 2.

Figure 2A:
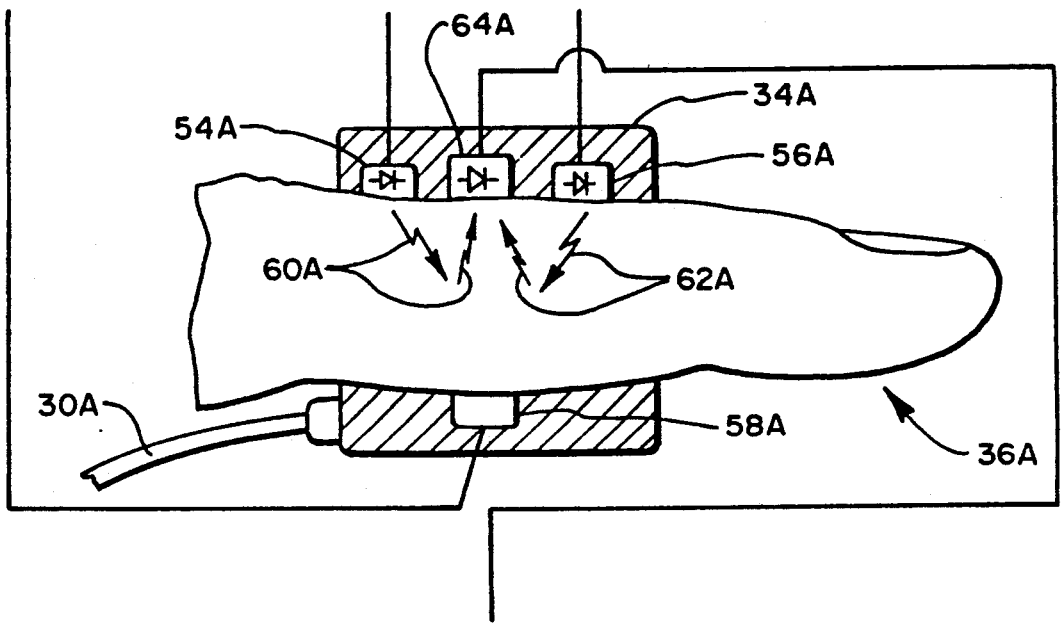
FIG. 2A is a cross sectional view of another preferred embodiment of the pressure cuff represented in FIG. 2.

Significantly, the inventive concepts taught herein may also be carried out by configuring the light emitting means and the photo detection means to operate in a reflective mode. A structure adapted for operating in a reflective mode is represented in FIG. 2A which is a cross sectional view showing LED 54A and LED 56A positioned within a pressure cuff 34A adjacent the photodiode 64A. Positioning the LEDs 354 and 56A adjacent to the photodiode 64A, or in another similar position, allows the photodiode 64A to receive that portion of the light beams reflected from the blood, tissue, and bone of the patient's finger 36A. It will be appreciated that it is necessary to operate the embodiment in such a reflective mode to best utilize body parts such as the patient's forehead as a sensing location.

Figure 5A:
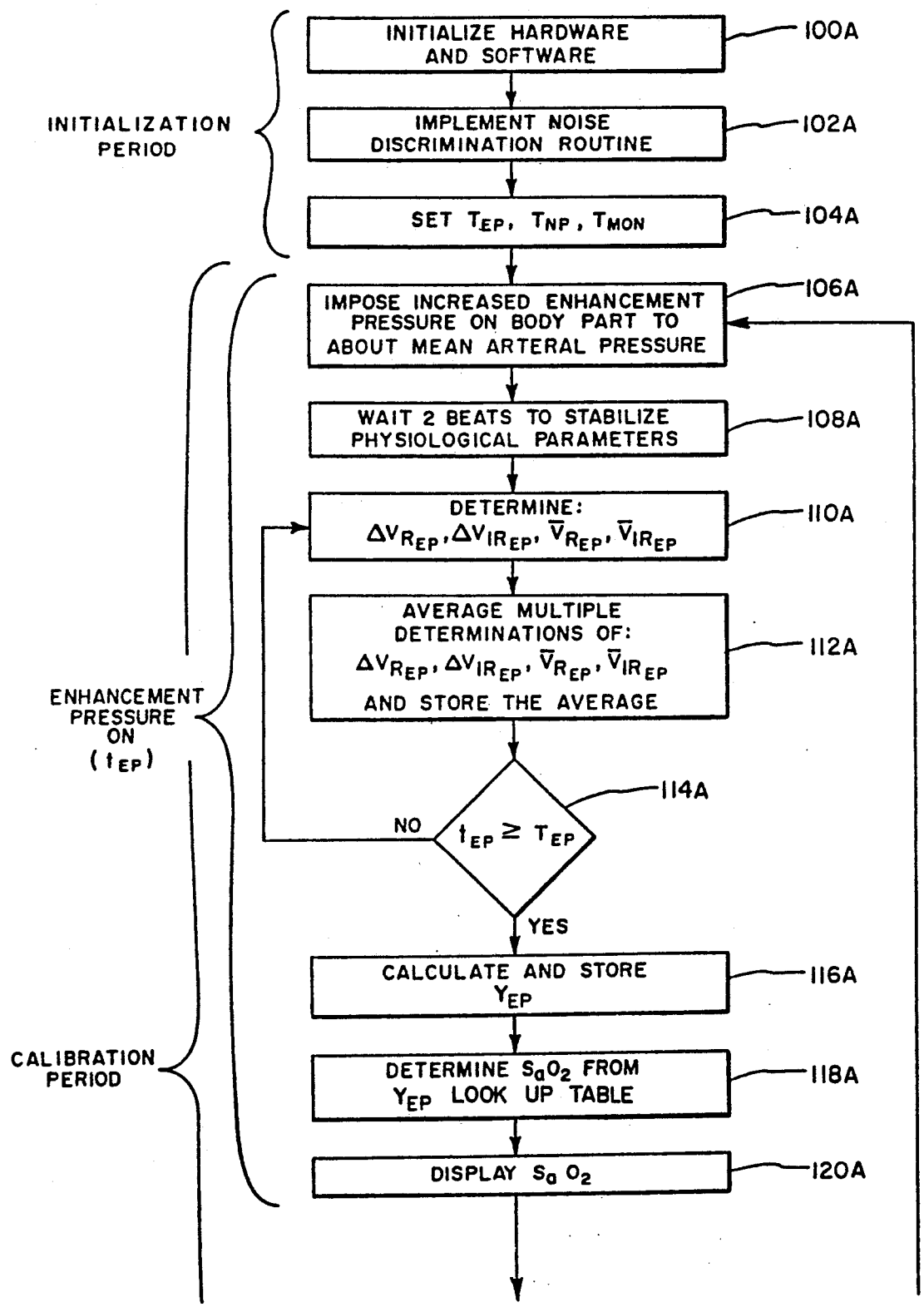
FIGS. 5A and 5B are flow charts representing the steps of another presently preferred method of the present invention for determining arterial blood oxygen saturation levels.
Figure 5B:
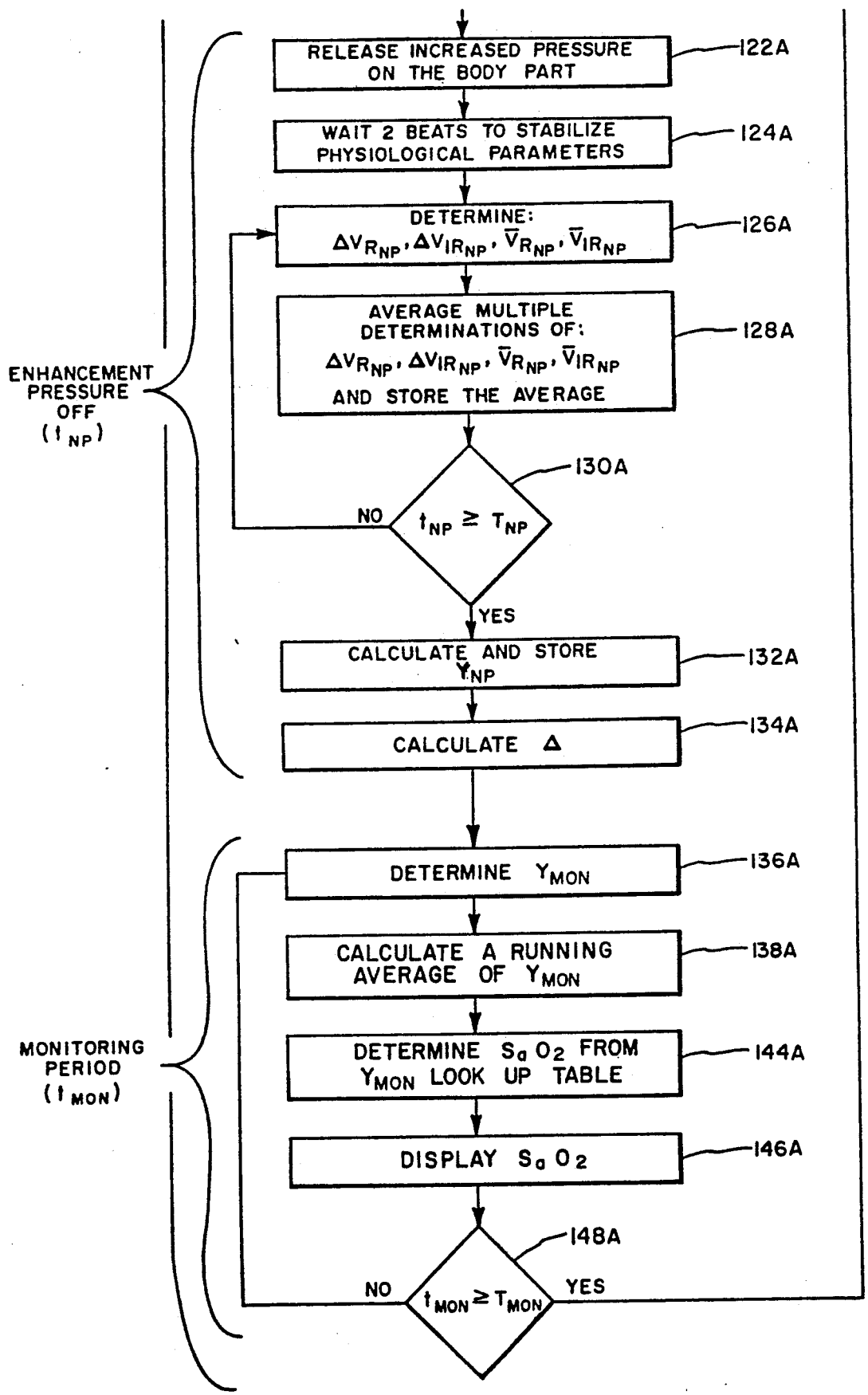

When an apparatus which embodies the inventive concepts taught herein is operated in a reflective mode, it is necessary to alter the method set forth in the flow charts of FIGS. 3A and 3B somewhat. Thus, the flow chart shown in FIGS. 5A and 5B provide the steps carried out when using the presently preferred structure represented in FIG. 2A.

Figure 2B:
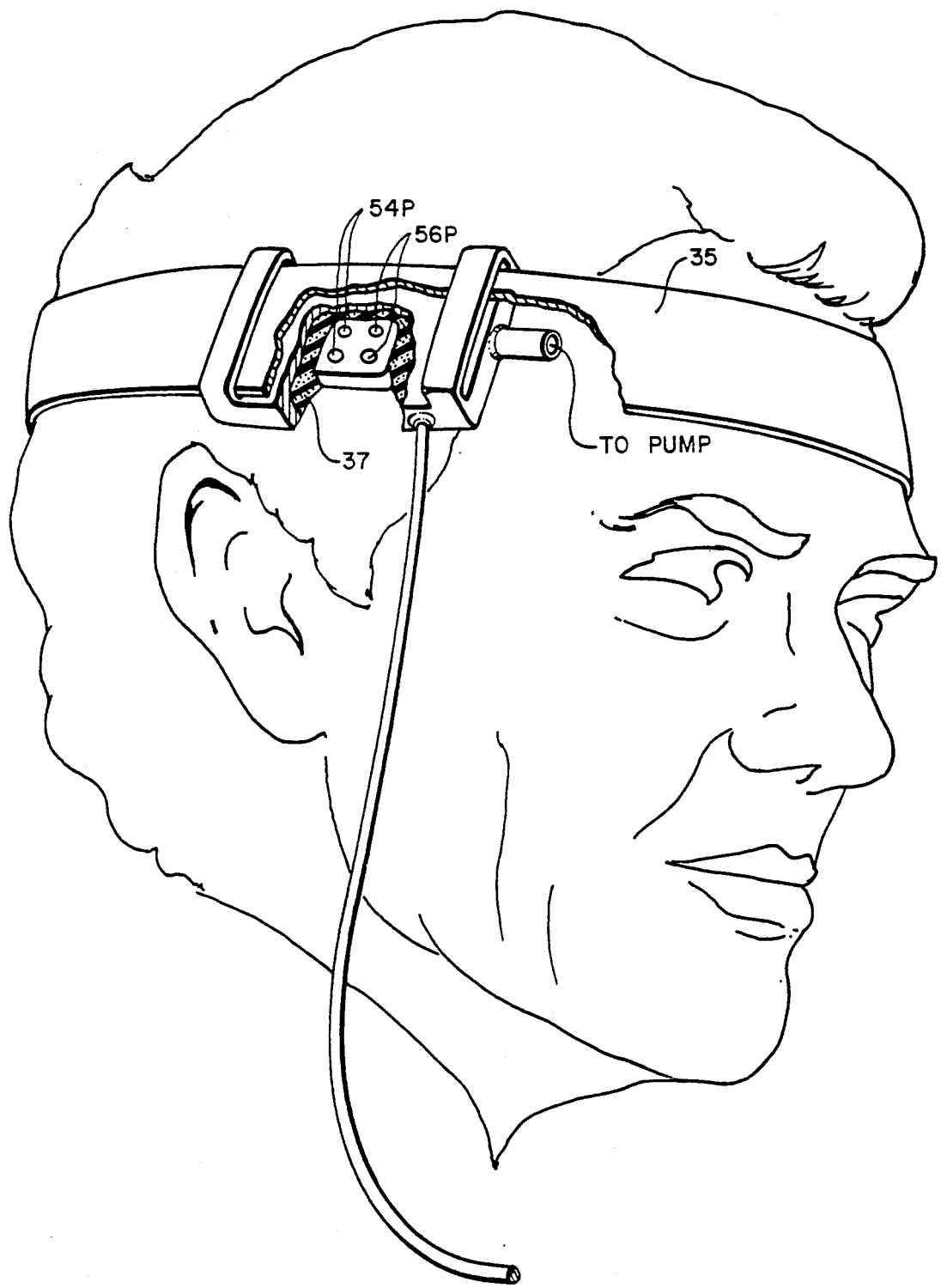
FIG. 2B is a partially cutaway perspective view of another presently preferred embodiment of the present invention positioned on a patient's forehead.

Another embodiment of the present invention operating in a reflective mode is shown in the partially cut away perspective view of FIG. 2B. As represented in FIG. 2B, embodiments of the present invention may be applied to the forehead of a patient. When used in this manner, the embodiment includes a means for positioning, for example an elastic strap 35, and a pressure generating device (such as an inflatable capsule illustrated at 37 in FIG. 2B) over the patient's forehead.

Also illustrated in FIG. 2B are two pairs of LEDs 54P and 56P. Providing two pairs of LEDs provides advantages in some situations. For example, in some situations the best signal to noise ratio may be obtained by using both pairs of LEDs or only two or three of the LEDs. The relationship of the LEDs to the photodetector may also be varied from that shown in FIG. 2B.

The steps shown in the flow chart of FIGS. 5A and 5B closely parallel the steps previously described in connection with FIGS. 3A and 3B except where departures are necessary to allow operation in a reflective mode. When the photodetector is positioned to receive light which is reflected from the patient's body part, it is necessary to calculate and store $Y_{EP}$ (rather than $RLOG_{EP}$ when operating in the transmission mode). A value for $Y_{EP}$ is derived from the stored average valves according to equation (8) provided below.

$$Y_{EP} = \frac{\Delta V_{REP}}{\bar{V}_{REP}} \qquad (8)$$

Those skilled in the art will appreciate that the calculation of $Y_{EP}$, and the other calculations represented in FIGS. 5A and 5B, may be readily carried out by a microcomputer as previously explained.

Once a value for $Y_{EP}$ is calculated and stored, the $S_aO_2$ corresponding to the calculated value of $Y_{EP}$ is found by reference to a $Y_{EP}$ look-up table as indicated at step 218A. The $Y_{EP}$ look-up table is derived from empirical data gathered during use of the system described herein. For example, once a red LED, infrared LED, photodiode, and other hardware items have been configured to provide the system described herein, the values obtained for YEP may be correlated with the $S_aO_2$ value obtained using another $S_aO_2$ determination method, for example, an in vitro method. Alternatively, the subject's $S_aO_2$ may be altered by altering the composition of the inspired gases and monitoring the composition of the expired gases. Once the $Y_{EP}$ look-up table has been completed, it can be used in the case of any number of patients if the performance of the apparatus hardware is maintained within appropriate parameters considering the effects of age, temperature, and variability of mass produced components.

The $S_aO_2$ which was determined from the $Y_{EP}$ lookup table at step 118A is displayed as represented at step 120A in FIG. 5A on the display means 42 represented in FIG. 2. It should be appreciated that the $S_1O_2$ value displayed at step 120A during the enhancement pressure on interval is more accurate and reliable than $SaO_2$ values provided by previously available pulse oximetry systems due to the enhancement of the arterial pulsatile signal output from the photodiode and the decrease of the capillary oxygen saturation contribution to the same signal.

Nevertheless, as explained previously, the interval during which the enhancement pressure is imposed must be limited due to several considerations including avoiding pain for the patient and affecting the physiology of the patient so that the measurements obtained are altered in any significant fashion. Thus, the enhancement pressure is released from the body part for the remainder of the calibration period and monitoring period as represented at step 122A as shown in FIG. 5B.

As shown in FIGS. 4a–4g, the enhancement pressure-off interval of the calibration period begins when the enhancement pressure is released and the pressure on the body part returns to the ambient pressure. Again, as represented at step 124A, it is necessary to wait at least two heartbeats before measuring any variables.

Continuing to refer to FIG. 5B and similarly to the steps taken during the enhancement pressure-on interval, the enhancement pressure-off interval includes steps to determine four variables as shown at step 126A. The same variables previously defined shown at step 126 in FIG. 3B have the same definition in the flow chart of FIGS. 5A and 5B when the embodiment operates in a reflective mode.

Also, similarly to the steps taken during the enhancement pressure-on interval, the average of multiple determinations of the enhancement pressure-off interval variables (step 128A) is calculated until the length of the enhancement pressure-off interval ($t_{NP}$) is equal to or greater than the time previously set for the enhancement pressure-off interval ($T_{NP}$) as represented at step 130A in FIG. 5B.

As represented in FIG. 5B, a value for $Y_{NP}$ is then obtained and stored at step 132A in accordance with equation (9) provided below.

$$Y_{NP} = \frac{\Delta V_{RNP}/V_{RNP}}{\Delta V_{IRNP}/V_{IRNP}} \quad (9)$$

Having calculated and stored both $Y_{EP}$ and $Y_{NP}$, $\Delta$ may be calculated according to equation (10).

$$\Delta = \frac{Y_{EP}}{Y_{NP} - 1} \quad (10)$$

Since $\Delta$ has been calculated in accordance with equation (10), corrections may be made to subsequent $S_aO_2$ measurements to account for the effect of $S_cO_2$ and to reduce or eliminate the contribution of $S_cO_2$ on the $S_aO_2$ level of the patient to be displayed. Having carried out these steps, the calibration period is complete.

The first step which takes place during the monitoring period ($t_{MON}$), shown at 136A in FIG. 5B, requires that $Y_{MON}$ be calculated according to equation (11) provided below.

$$Y_{MON} = \frac{\Delta V_{RMON}/V_{RMON}}{\Delta V_{IRMON}/V_{IRMON}} (1 - \Delta) \quad (11)$$

Next, at step 138A, a running average of $Y_{MON}$ is calculated.

Having calculated an average value of $Y_{MON}$, the $S_aO_2$ level may be determined by obtaining a value from the $Y_{MON}$ look-up table as represented at step 144A. The $Y_{MON}$ look-up table is derived in an empirical fashion similar to the fashion described for the $Y_{EP}$ look-up table. Significantly, the value obtained from the $Y_{MON}$ look-up table represents the $S_aO_2$ value since the $S_cO_2$ contribution has already been "calibrated out" in previous steps. The value obtained from the $Y_{MON}$ look-up table is displayed as represented at step 146A. As shown at step 148A, the steps of the monitoring period are repeated until $t_{MON} \geq T_{MON}$.

As indicated previously, the system represented in FIGS. 2 and 2A includes all the hardware necessary to carry out blood pressure determinations as described and claimed in U.S. patent application Ser. No. 07/068,107 which was previously incorporated herein by reference.

As set forth in the aforementioned application, two of the three parameters (mean arterial pressure and systolic arterial pressure) may be measured using the widely known oscillometric method and the third parameter (diastolic arterial pressure) may be calculated using a recursive procedure wherein an estimate of the diastolic pressure is made and the estimated diastolic pressure, and the other parameters set forth earlier, are used in Hardy model calculations. If the estimate was correct, the calculated mean arterial pressure will agree with the measured arterial pressure. Once all three parameters have been determined, the Hardy model compliance curve can be used to continuously calculate a blood pressure waveform using the $V_R$ or the $V_{IR}$ signal. It will be appreciated that the signal produced by either the red or the infrared LED can be used to detect volume changes in the arteries being examined. With the relative changes in volume being available by examining the $V_R$ or the $V_{IR}$ signal, the pressure-volume relationship of the artery described by the Hardy model allows the pressure waveform to be calculated.

As in the case of the enhanced pulse oximetry method described herein, it is necessary to regularly calibrate the values used in the blood pressure determinations due to changes in the physiology of the patient.

In most cases, it is generally not necessary to conduct a complete oscillometric determination of both systolic and mean arterial pressures as often as it is necessary to begin a calibration period for $S_aO_2$ determinations. Thus, the period during which the oscillometric determination is carried out is referred to as a "super calibration period." It should be understood that the oscillometric method requires that the artery be completely occluded and thus whatever means which is used to impose the enhancement pressure on the body part should be capable of imposing such a pressure. Also, because the pressure imposed is greater than the systolic pressure, it may require that an appropriate waiting period be provided before $S_aO_2$ determinations can be reliably made.

Significantly, the enhancement pressure, which equals the mean arterial pressure, is applied during every calibration period for $S_aO_2$ determinations. This allows the measured mean arterial pressure to be compared to the mean arterial pressure being used in the Hardy model calculations and, if a significant discrepancy between the two is found, a super calibration period may be begun.

It will thus be appreciated that the present invention provides a great advantage in allowing both arterial oxygen and blood pressure determinations to be made using little more hardware than that which is required for determining arterial oxygen levels. Also, the present invention is able to distinguish arterial oxygen saturation levels from capillary oxygen saturation levels and to provide arterial oxygen saturation level determinations which are more accurate and reliable than those available from previously known oximetry systems.

The invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A system for enhancing noninvasive monitoring of a patient's arterial oxygen saturation level, said system comprising:
   light means for passing at least a first light beam and a second light beam into a body part of said patient containing both arterial and nonarterial blood vessels;
   detection means for detecting relative amounts of each said light beam absorbed by blood in the blood vessels;
   enhancement means for increasing the absorption of the light beams by blood in the arterial blood vessels in relation to blood in the nonarterial blood vessels; processor means, electronically coupled to the light means, the detection means and the enhancement means, for coordinating the operation of each said means in relation to one another, and for deriving from the detected relative amounts of each said light beam an arterial oxygen saturation level; and
   display means, electronically coupled to the processor means, for outputting a visually perceptible indication of the arterial oxygen saturation level.

2. A system as defined in claim 1 wherein the light means comprises first and second light-emitting diodes which produce first and second light beams in the visible and infrared light regions, respectively, and wherein the enhancement means comprises a pressure generating device, the pressure generating device being operative to impose a pressure on the body part for at least a part of the time that the light beams are passing into the blood vessels.

3. A system as defined in claim 2 wherein the light means further comprises:
   driver means for driving the light emitting diodes; and
   multiplexing means for selectively connecting the driver means to one of the light emitting diodes.

4. A system as defined in claim 2 wherein said detection means comprises:
   a semiconductor photodetection device for providing an output signal proportional to the intensity of light beams striking the photodetection device;
   a gain control amplifier for controlling the gain of the output signal; and
   multiplexing means for directing the output signal to one of a plurality of channels provided in the processor means.

5. A system as defined in claim 1 wherein the light means comprises a first solid-state device emitting a light beam having a wavelength in the range from about 600 nanometers to about 725 nanometers and a second solid-state device emitting a light beam having a wavelength in the range from about 875 nanometers to about 1,000 nanometers.

6. A system as defined in claim 1 wherein the light means comprises a first light source emitting a light beam having a first wavelength which is substantially equally absorbed by oxyhemoglobin and reduced hemoglobin, the light means further comprising a second light source emitting a light beam having a second wavelength which is absorbed unequally by oxyhemoglobin and reduced hemoglobin.

7. A system as defined in claim 4 wherein the enhancement means comprises a pressure cuff.

8. A system as defined in claim 5 wherein the first light source comprises a first pair of solid state light emitting devices and wherein the second light source comprises a second pair of solid state light emitting devices, each pair of light emitting devices including an infrared light emitting source and a red light emitting source, each pair of the light emitting devices positioned on the interior of the pressure cuff and wherein the detection means comprises a solid-state photodetection device positioned on the interior of the pressure cuff.

9. A system as defined in claim 1 wherein the enhancement means comprises an inflatable pressure generating device and means for positioning the inflatable pressure generating device around the patient's body part.

10. A system as defined in claim 1 wherein said enhancement means comprises a pressure imposing device and means for varying the pressure within the pressure imposing device.

11. A system as defined in claim 10 further comprising means for sensing the pressure within the pressure imposing device.

12. A system as defined in claim 11 wherein the means for sensing the pressure comprises a pressure transducer.

13. A system as defined in claim 1 wherein the processor means comprises a microprocessor which controls the operation of the light means and the enhancement means.

14. A system as defined in claim 1 further comprising at least one analog to digital converter connected to the detection means and to the processor means, to digitize the signal output from the detecting means and input the signal to the processor means.

15. A system as defined in claim 1 wherein said system is also used for monitoring of the patient's arterial blood pressure waveform, and:
   wherein the light means and the detection means together generate a first electrical signal proportional to the relative volume of said arterial blood vessels, the first signal being output by the detection means;
wherein the enhancement means comprises pressure means, the pressure means being in physical proximity with the light means, the pressure means periodically imposing a pressure on the body part;
wherein said system further comprises pressure transducer means for detecting the pressure imposed on the body part and for outputting a second electrical signal proportional to the pressure;
wherein the processor means comprises means for deriving from the first and second electrical signals the patient's arterial blood pressure waveform; and
wherein the display means comprises means for providing a visually perceptible indication of the arterial pressure waveform in addition to the indication of arterial oxygen saturation level.

16. A monitoring system for enhanced noninvasive monitoring of a patient's arterial oxygen saturation level, said system comprising:
light means for periodically directing a first light beam and a second light beam into both capillary and arterial blood vessels contained in a patient's body part;
pressure means for imposing a pressure on the patient's body part to increase the absorption of at least one of the light beams by blood in the arterial blood vessels in relation to blood in the nonarterial blood vessels, the light means being connected to the pressure means such that the first and second light beans are directed into the body part upon which the pressure is imposed by the pressure means;
detection means for detecting relative amounts of each said light beam absorbed by arterial blood within the body part;
processor means, electronically coupled to the pressure means and the detection means, for (a) controlling the pressure means so as to cause the pressure to be imposed on the body part for at least a portion of the time that the light beams are passing into the body part, and for (b) deriving from the detected relative amounts of each said light beam an arterial oxygen saturation level; and
display means, electronically coupled to the processor means, for outputting a visually perceptible indication of the arterial oxygen saturation level.

17. A monitoring system as defined in claim 16 wherein the light means comprises a first solid state device adapted for emitting the first light beam, the first light beam having a wavelength substantially within the visible red portion of the spectrum.

18. A monitoring system as defined in claim 17 wherein the light means further comprises a second solid state device adapted for emitting the second light beam, the second light beam having a wavelength substantially within the infrared portion of the spectrum.

19. A monitoring system as defined in claim 18 further comprising means for time multiplexing the first and the second light beams such that the first and second light beams are alternately directed into the body part.

20. A monitoring system as defined in claim 16 wherein the detection means comprises a solid state photodetection device.

21. A monitoring system as defined in claim 20 wherein the photodetection device is positioned on a pressure imposing surface of the pressure means.

22. A monitoring system as defined in claim 21 wherein the pressure means comprises a pressure cuff and the photodetection device is positioned substantially opposite from the position of the light means such that the first and second light beams transmitted through the body part are detected by the photodetection device.

23. A monitoring system as defined in claim 21 wherein the photodetection device is positioned to be substantially adjacent the light means such that the first and second light beams reflected from the body part are detected by the photodetection device.

24. A monitoring system as defined in claim 21 wherein the pressure means comprises means for shielding the photodetection device from ambient light.

25. A monitoring system as defined in claim 16 wherein the processor means comprises a microcomputer.

26. A monitoring system as defined in claim 25 further comprising at least one analog to digital converter connected to the detection means and to the processor means to digitize the output from the detection means and input said output to the processor means.

27. A monitoring system as defined in claim 16 wherein the display means comprises a numeric digital display.

28. A monitoring system as defined in claim 16 wherein the display means comprises a video display.

29. A monitoring system as defined in claim 16 wherein the processor means further comprises means for deriving the patient's blood pressure from the amounts of light detected by the detection means.

30. A monitoring system as defined in claim 29 wherein the display means comprises means for displaying the patient's systolic, diastolic, and means arterial blood pressures.

31. A system as defined in claim 29 further comprising means for sensing the pressure within the pressure means.

32. A system as defined in claim 31 wherein the means for sensing the pressure comprises a pressure transducer.

33. A system as defined in claim 16 wherein the pressure means comprises a pressure cuff which includes means for positioning the pressure cuff on the patient's finger.

34. A system as defined in claim 16 wherein the pressure means comprises a pressure cuff which includes means for positioning the pressure cuff on the patient's toe.

35. A system as defined in claim 16 wherein the pressure means comprises an inflatable pressure generating device and means for positioning the inflatable pressure generating device on the patient's forehead.

36. A monitoring system for enhanced noninvasive monitoring of a patient's arterial oxygen saturation level, the system comprising:
pressure means for imposing a pressure on a patient's body part, the pressure means steadily imposing a pressure which is less than completely occlusive to both arterial and capillary blood vessels contained in the body part and which is great enough to substantially increase the volume changes of the pulsing arterial vessels;
first light means and second light means for periodically directing first and second light beams in the visible red and infrared light spectra, respectively, into arterial and capillary blood vessels contained in the body part;

transducer means for detecting relative amount of the first and second light beams absorbed by the blood after being directed into the capillary and arterial blood vessels, the transducer means connected to the pressure means such that the transducer means only receives the first and second light beams which have passed through the body part which is intermittently imposed upon by the pressure means;

processor means, electronically coupled to the pressure means for (a) controlling the pressure means so as to cause the pressure to be intermittently imposed on the body part as the first and second light beams are passing into the body part, whereby absorption of said light beams by arterial blood is increased relative to absorption by non-arterial blood, and for (b) deriving from the detected relative amount of the first and second light beams absorbed by the arterial blood an arterial oxygen saturation level; and display means, electronically coupled to the processor means, for outputting a visually perceptible indication of the arterial oxygen saturation level.

37. A monitoring system as defined in claim 36 wherein the transducer means comprises means for receiving the first and second light beams and outputting an electrical signal proportional to the intensity of the light beams.

38. A monitoring system as defined in claim 36 wherein the transducer means comprises a solid state photoelectric transducer which is in physical proximity with said pressure means.

39. A monitoring system as defined in claim 38 wherein the pressure means further comprises means for shielding said solid state photoelectric transducer from ambient light.

40. A monitoring system as defined in claim 36 wherein the pressure means further comprises pressure transducer means for sensing the pressure imposed on the body part connected to the processor means and wherein the processor means is further for (c) deriving from the light detected by the transducer means the patient's systolic and diastolic blood pressure.

41. A monitoring system as defined in claim 40 wherein the display means includes means for outputting a visually perceptible indication of the patient's systolic and diastolic blood pressure.

42. A system as defined in claim 36 wherein the pressure means comprises a pressure cuff which includes means for positioning the pressure cuff on the patient's finger.

43. A system as defined in claim 36 wherein the pressure means comprises a pressure cuff which includes means for positioning the pressure cuff on the patient's toe.

44. A system as defined in claim 36 wherein the pressure means comprises an inflatable pressure generating device and means for positioning the inflatable pressure generating device on the patient's forehead.

45. A noninvasive monitoring system for providing an indication of both a patient's arterial blood pressures and arterial oxygen saturation level, the system comprising:

light means for passing first and second light beams into a body part of the patient containing both arterial and nonarterial blood vessels, the first and second light beams having wavelengths in the visible and infrared portions of the spectrum, respectively;

pressure means, for periodically imposing an increased pressure on the body part, said pressure means being associated with said light means and normally nonocclusive in relation to the blood vessels;

light detection means for detecting relative amounts of the first and second light beams reflected by and transmitted through arterial blood vessels and for outputting first and second electric signals proportional to the detected amounts of the first and second light beams respectively, at least one of the signals being proportional to relative volume of said arterial blood vessels;

pressure detection means for detecting the pressure imposed on the body part by the pressure means and for outputting a third electric signal proportional to the increased pressure;

processor means for receiving the first, second and third electric signals, the processor means comprising means for deriving arterial pressures and for deriving an oxygen saturation level from said electric signals; and display means, electronically coupled to the processor means, for outputting visually perceptible indications of the patient's arterial pressure waveform and oxygen saturation level.

46. A noninvasive monitoring system as defined in claim 45 wherein the pressure means comprises a cylindrical pressure cuff.

47. A noninvasive monitoring system as defined in claim 45 wherein the light means comprises first and second light-emitting diodes.

48. A noninvasive, monitoring method for determining the arterial oxygen blood saturation level in a patient's body part containing both arterial and nonarterial blood vessels, the method comprising the steps of:

(a) directing a first and a second light beam in the body part, the first and second light beams having different wavelengths;

(b) imposing an enhancement pressure on the body part, said enhancement pressure being less than a completely occlusive pressure and great enough so as to substantially increase the compliance of the arterial vessels contained in the body part thereby increasing arterial pulses;

(c) detecting the relative amounts of the first and second light beams absorbed by the blood contained in the arterial vessels;

(d) determining the arterial oxygen saturation level in the body part by the detected amounts of the first and second light beams; and (e) displaying a value representing the determined arterial oxygen saturation level.

49. A noninvasive, monitoring method as defined in claim 48 further comprising the steps of determining the patient's mean arterial pressure by changing the pressure imposed on the body part until the modulation of the first light beam by the pulsing of the arterial blood vessels is maximized and determining the pressure imposed on the body part at the time the modulation of the first light beam is maximized.

50. A noninvasive, monitoring method as defined in claim 48 wherein the step of imposing an enhancement pressure on the body part comprises the step of imposing a pressure circumferentially about the patient's finger.

51. A noninvasive, monitoring method as defined in claim 48 wherein the step of imposing an enhancement pressure on the body part comprises the step of imposing a pressure circumferentially about the patient's toe.

52. A noninvasive, monitoring method as defined in claim 48 wherein the step of imposing an enhancement pressure on the body part comprises the step of imposing a pressure upon the patient's forehead.

53. A noninvasive, monitoring method as defined in claim 48 wherein the step of directing a first and a second light beam into the body part comprises the step of alternatively directing a first light beam having a wavelength in the visible red region into the body part and directing a second light beam having a wavelength in the infrared region into the body part.

54. A noninvasive, monitoring method as defined in claim 48 wherein the step of detecting the relative amounts of the first and second light beams absorbed comprises the step of detecting the relative amounts of the first and second light beams which are reflected from the body part.

55. A noninvasive, monitoring method as defined in claim 48 wherein the step of detecting the relative amounts of the first and second light beams absorbed comprises the step of detecting the relative amounts of the first and second light beams which are transmitted through the body part.

56. A noninvasive, monitoring method as defined in claim 48 wherein the step of detecting the relative amounts of the first and second light beams absorbed by the body part comprises the steps of:
positioning at least one photodetector adjacent to the body part; and
outputting a voltage from the photodetector which is proportional to the amounts of the first and second light beams which strike the photodetector.

57. A noninvasive, monitoring method as defined in claim 56 wherein the step of determining the arterial oxygen saturation level comprises the step of comparing a value representing the amount of the first and the second light beams absorbed by the body part to values contained in an empirically developed look-up table to find the oxygen saturation level which corresponds to the value of the voltage output.

58. A noninvasive method for monitoring a patient's arterial oxygen saturation level, the method comprising the steps of:
(a) establishing a calibration interval comprised of the following steps:
(1) directing a first light beam and a second light beam into a body part of the patient containing at least one arterial and at least one nonarterial blood vessel, the first light beam having a first wavelength and the second light beam having a different, second wavelength;
(2) imposing a first pressure to the body part such that the arterial blood vessel located therein is at least partially unloaded;
(3) detecting the amount of light from the first light beam and from the second light beam which is absorbed by said body part;
(4) determining from said detected amount of the first and second light beams the arterial oxygen saturation level in the body part;
(5) releasing the first pressure from the body part;
(6) detecting the amount of light from the first light beam and from the second light beam which is absorbed by the body part after the first pressure is released;
(7) determining a calibration factor derived from the differences in the amount of the first and second light beams which were detected when the first pressure was applied to, and released from, the body part, the calibration factor representing the contribution of non-arterial blood oxygen saturation to the amount of light detected;
(b) establishing a monitoring interval by continuing to detect the amount of the first and second light beams which are absorbed by the body part after the calibration factor is determined;
(c) calculating during the monitoring interval the oxygen saturation level of the arterial blood using the calibration factor; and
(d) displaying the oxygen saturation level on a visual display.

59. A noninvasive method for monitoring a patient's arterial oxygen saturation level as defined in claim 58 further comprising the step of repeatedly beginning a calibration interval followed by a monitoring interval.

60. A noninvasive method for monitoring a patient's arterial oxygen saturation level as defined in claim 58 wherein the first pressure is about equal to the patient's mean arterial pressure.

61. A noninvasive method for monitoring a patient's arterial oxygen saturation level as defined in claim 58 wherein the calibration interval is less than one third the length of the monitoring interval.

62. A noninvasive method for monitoring a patient's arterial oxygen saturation level as defined in claim 58 wherein the first wavelength is in the infrared portion of the spectrum and the second wavelength is in the visible red portion of the spectrum.

63. A noninvasive method for monitoring a patient's arterial oxygen saturation level as defined in claim 60 further comprising a method for noninvasively monitoring the patient's blood pressure, the method further comprising the steps of:
measuring the body part's systolic and mean arterial pressure using an oscillometric method;
detecting the change in volume of the patient's blood vessel by the change in intensity of one of the light beams;
estimating a diastolic pressure;
calculating a mean arterial pressure using the Hardy model equation which relates arterial volume to arterial pressure and the estimated diastolic pressure;
comparing the calculated mean arterial pressure and the measured mean arterial pressure;
estimating the diastolic pressure and recalculating the mean arterial pressure until the two values agree within a predetermined standard; and
displaying the measured systolic and the most recently estimated diastolic blood pressure on a visual display.

64. A noninvasive method for monitoring a patient's arterial oxygen saturation level and blood pressure as defined in claim 65 further comprising the step of deriving and continually displaying the patient's blood pressure waveform from the measured systolic and most recently estimated diastolic blood pressure.

65. A noninvasive method for monitoring a patient's oxygen saturation level as defined in claim 58 wherein the step of detecting the amount of light from the first light beam and from the second light beam comprises the step of detecting the amount of light from the first light beam and from the second light beam which are reflected from the body part.

66. A noninvasive method for monitoring a patient's oxygen saturation level as defined in claim 58 wherein the step of detecting the amount of light from the first light beam and the second light beam comprises the step of detecting the amount of light from the first light beam and from the second light beam which are transmitted through the body part.

67. A method for noninvasively determining a patient's arterial oxygen saturation level, the method comprising the steps of:
  (a) imposing an enhancement pressure on a body part containing both arterial and nonarterial blood vessels so as to significantly increase the pulsation by the arterial blood vessels in the body part;
  (b) directing a first and a second light beam into the body part, the first and second light beams having different wavelengths;
  (c) detecting the amounts of the first and second light beams absorbed by the arterial blood;
  (d) determining the arterial oxygen saturation level in the body part from the detected amounts of the first and second light beams;
  (e) displaying the arterial oxygen saturation level;
  (f) releasing the enhancement pressure from the body part;
  (g) detecting the relative amounts of the first and second light beams absorbed by the arterial and nonarterial blood in the body part;
  (h) determining the relative contribution to said absorption attributable to the arterial blood with respect to the total of the amount of the first and second light beams which are detected; and
  (i) displaying an oxygen saturation level corresponding to substantially only the contribution of the arterial blood to the detected amounts of the first and second light beams when the enhancement pressure is removed.

68. A method for noninvasively determining a patient's arterial oxygen saturation level as defined in claim 67 wherein the step of imposing an enhancement pressure on a body part comprises the step of imposing a pressure approximately equal to the body part's mean arterial pressure circumferentially about one of the patient's digits and wherein the step of detecting the amounts of the first and second light beams absorbed by the arterial blood comprises the step of detecting with a phototransducer device the amount of the first and second light beams transmitted through the patient's digit.

69. A method for noninvasively determining a patient's arterial oxygen saturation level as defined in claim 67 wherein the step of detecting the amounts of the first and second light beams absorbed by the arterial blood comprises the step of detecting with a phototransducer device the amount of the first and second light beams reflected from the body part.

70. A method for noninvasively determining a patient's arterial oxygen saturation level as defined in claim 67 wherein the step of determining the arterial oxygen saturation level in the body part comprises the step of comparing the amount of the first and second light beams which are absorbed with a set of predetermined look-up table values and deriving from the lookup table values an arterial oxygen saturation level and wherein the step of displaying the arterial oxygen saturation level comprises the step of outputting the arterial oxygen saturation level to a visually perceptible display.

71. A method for noninvasively determining a patient's arterial oxygen saturation level as defined in claim 67 further comprising the step of repeating steps (g) through (i) a multiplicity of times before repeating steps (a) through (f).

72. A noninvasive method for continuously monitoring a patient's arterial oxygen saturation and arterial blood pressure waveform, the method comprising:
  imposing an occlusive pressure on a patient's body part containing both arterial and nonarterial blood vessels;
  directing at least a first light beam into the body part;
  gradually releasing the occlusive pressure;
  detecting when a pulsatile signal first modulates the first light beam;
  measuring the occlusive pressure imposed on the body part when the pulsatile signal first modulates the first light beam and storing the value of the pressure as the systolic pressure;
  releasing the occlusive pressure;
  imposing an enhancement pressure on the body part such that the modulation of the first light beam is substantially maximized to determine a measured mean arterial pressure;
  estimating an arterial diastolic pressure; calculating a mean arterial pressure using the estimated diastolic pressure, the measured systolic pressure, the detected amounts of the first light beam, and a formula which relates arterial pressure to arterial volume;
  comparing the calculated mean arterial pressure to the measured mean arterial pressure and displaying at least the diastolic pressure if the measured mean arterial pressure and the calculated arterial pressure agree within predetermined limits;
  directing a second light beam into the body part while the enhancement pressure is imposed on the first and second light beams having different wavelengths;
  detecting the relative amounts of the first and second light beams absorbed by the arterial blood contained in the body part;
  deriving an arterial oxygen saturation level from the detected amounts of the first and second light beams;
  releasing the enhancement pressure from the body part;
  calculating at least a new systolic and diastolic arterial blood pressure based upon the changes in the detected amount of the first light beam representing volume changes in the arteries contained in the body part while all pressure is released from the body part;
  detecting the relative amounts of the first and second light beams absorbed by the arterial and nonarterial blood vessels contained in the body part while all pressure is removed;
  determining the contribution of the arterial blood vessels to the detected amount of the first and second light beam so that the arterial oxygen saturation level may be determined; and
  displaying the arterial oxygen saturation level and the systolic and diastolic arterial blood pressure of the body part on a visually perceptible display.

* * * * *